US010194968B2

(12) United States Patent
Crawford et al.

(10) Patent No.: US 10,194,968 B2
(45) Date of Patent: Feb. 5, 2019

(54) SURGICAL ROD BENDING SYSTEM AND METHOD

(71) Applicant: DIGNITY HEALTH, San Francisco, CA (US)

(72) Inventors: Neil R. Crawford, Tempe, AZ (US); Nicholas Theodore, Paradise Valley, AZ (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 15/839,319

(22) Filed: Dec. 12, 2017

(65) Prior Publication Data

US 2018/0098805 A1 Apr. 12, 2018

Related U.S. Application Data

(62) Division of application No. 14/649,018, filed as application No. PCT/US2013/070773 on Nov. 19, 2013, now Pat. No. 9,872,715.

(Continued)

(51) Int. Cl.
| | |
|---|---|
| *A61B 17/88* | (2006.01) |
| *B21D 43/00* | (2006.01) |
| *B21D 7/08* | (2006.01) |
| *B21D 7/12* | (2006.01) |
| *B21D 7/14* | (2006.01) |
| *B21F 45/00* | (2006.01) |
| *B21F 1/00* | (2006.01) |
| *A61B 17/70* | (2006.01) |

(52) U.S. Cl.
CPC ............ *A61B 17/8863* (2013.01); *B21D 7/12* (2013.01); *B21D 7/14* (2013.01); *B21D 43/006* (2013.01); *B21F 45/008* (2013.01); *A61B 17/7013* (2013.01); *B21D 7/08* (2013.01); *B21F 1/008* (2013.01)

(58) Field of Classification Search
CPC .......... B21D 7/02; B21D 7/021; B21D 7/022; B21D 7/024; B21D 7/025; B21D 7/06; B21D 7/08; B21D 7/085; B21D 7/12; B21D 7/14; B21D 9/10; B21D 11/10; B21D 11/22; B21D 43/003; B21D 43/006; B21F 1/004; B21F 1/006; B21F 1/008; B21F 23/005; B21F 45/08; A61B 17/7013; A61B 17/8863
See application file for complete search history.

(56) References Cited

U.S. PATENT DOCUMENTS

| | | | |
|---|---|---|---|
| 3,661,002 | A | 5/1972 | Peddinghaus, Jr. |
| 3,821,525 | A | 6/1974 | Eaton et al. |

(Continued)

*Primary Examiner* — Peter DungBa Vo
*Assistant Examiner* — Joshua D Anderson
(74) *Attorney, Agent, or Firm* — Quarles & Brady LLP

(57) ABSTRACT

A system and method for bending a surgical rod using an automated bending system includes receiving an indication of a plurality of line segments defined on the rod and an indication of an angle measurement to be formed between at least two adjacent ones of the plurality of line segments. Bending parameters to perform on the rod to form the angle measurement between the at least two adjacent ones of the plurality of line segments are determined and operation of the automated bending system is controlled using the bending parameters to create an angle having the angle measurement between the at least two adjacent ones of the plurality of line segments.

20 Claims, 31 Drawing Sheets

Related U.S. Application Data

(60) Provisional application No. 61/733,752, filed on Dec. 5, 2012.

(56) References Cited

U.S. PATENT DOCUMENTS

| | | | |
|---|---|---|---|
| 4,785,650 | A | 11/1988 | Lusty |
| 4,799,373 | A | 1/1989 | Benton |
| 4,825,678 | A | 5/1989 | Post |
| 5,447,432 | A | 9/1995 | Andreiko et al. |
| 5,658,286 | A | 8/1997 | Sava |
| 5,938,662 | A | 8/1999 | Rinner |
| 6,035,691 | A | 3/2000 | Lin et al. |
| 6,434,995 | B1 | 8/2002 | Kataoka et al. |
| 7,957,831 | B2 | 6/2011 | Isaacs |
| 2004/0072120 | A1 | 4/2004 | Lauren |
| 2005/0262911 | A1 | 12/2005 | Danokwicz et al. |
| 2007/0227216 | A1 | 10/2007 | Schalliol |
| 2009/0249851 | A1 | 10/2009 | Isaacs |
| 2011/0295086 | A1 | 12/2011 | Nakada et al. |

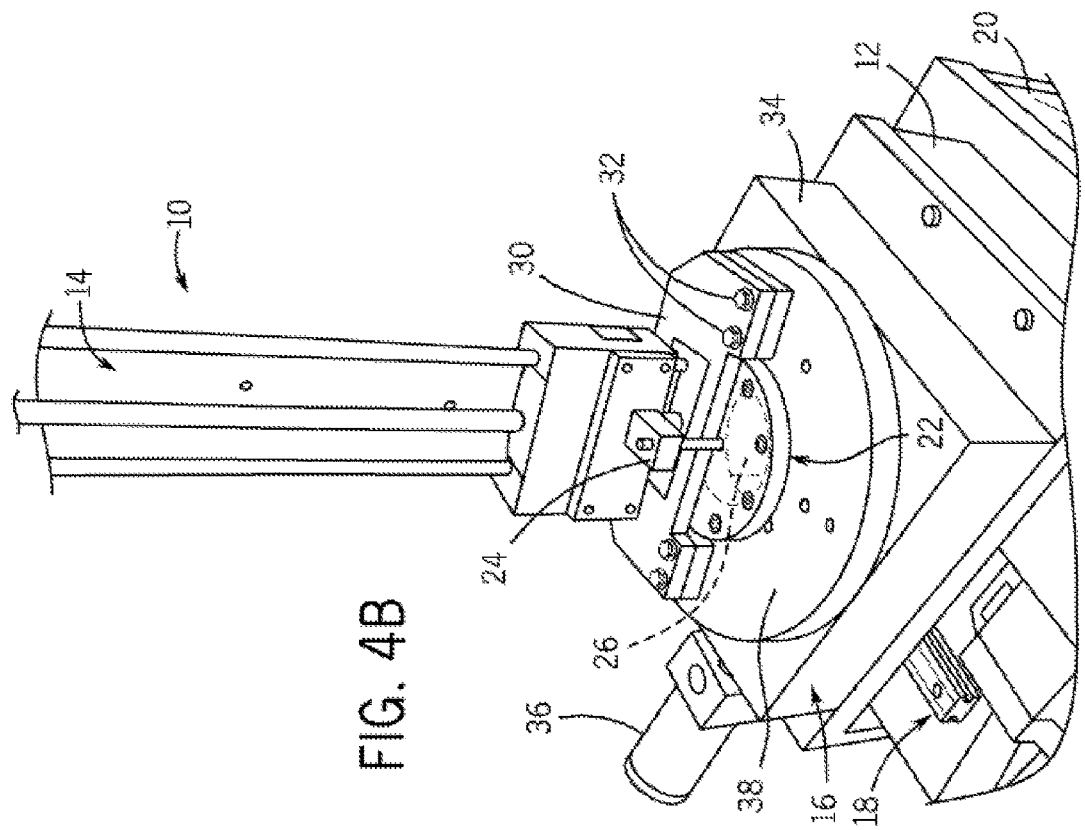
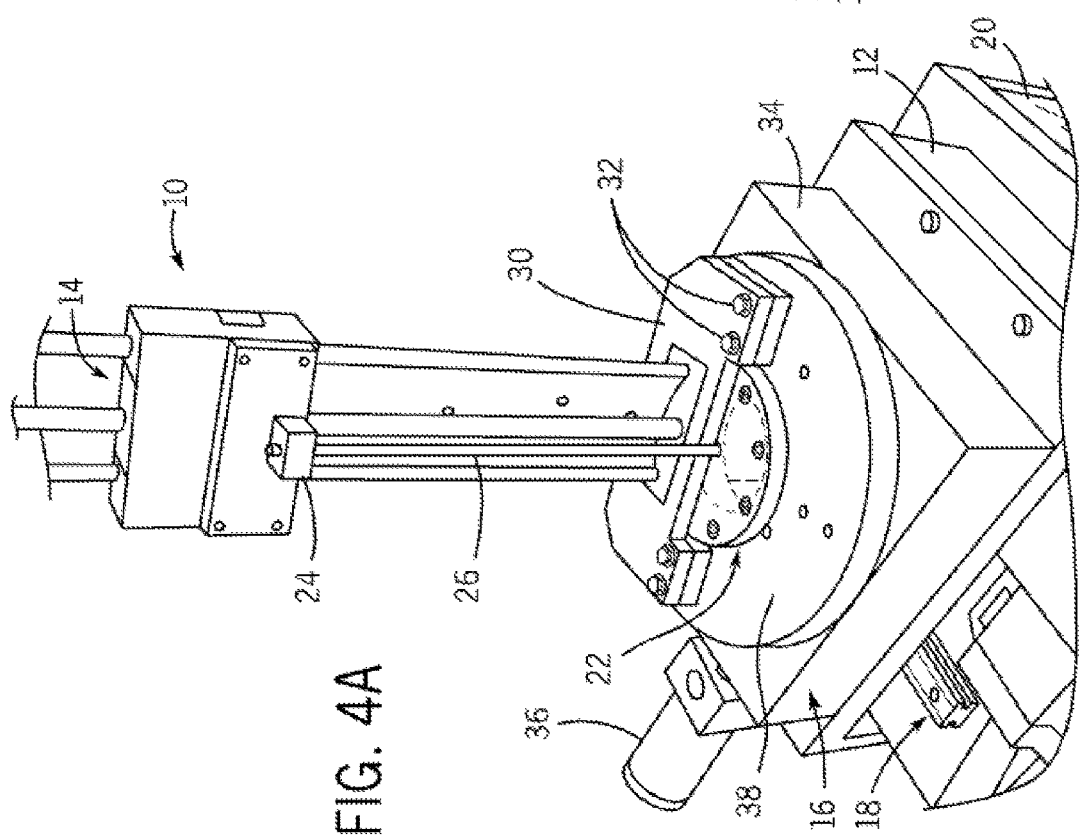

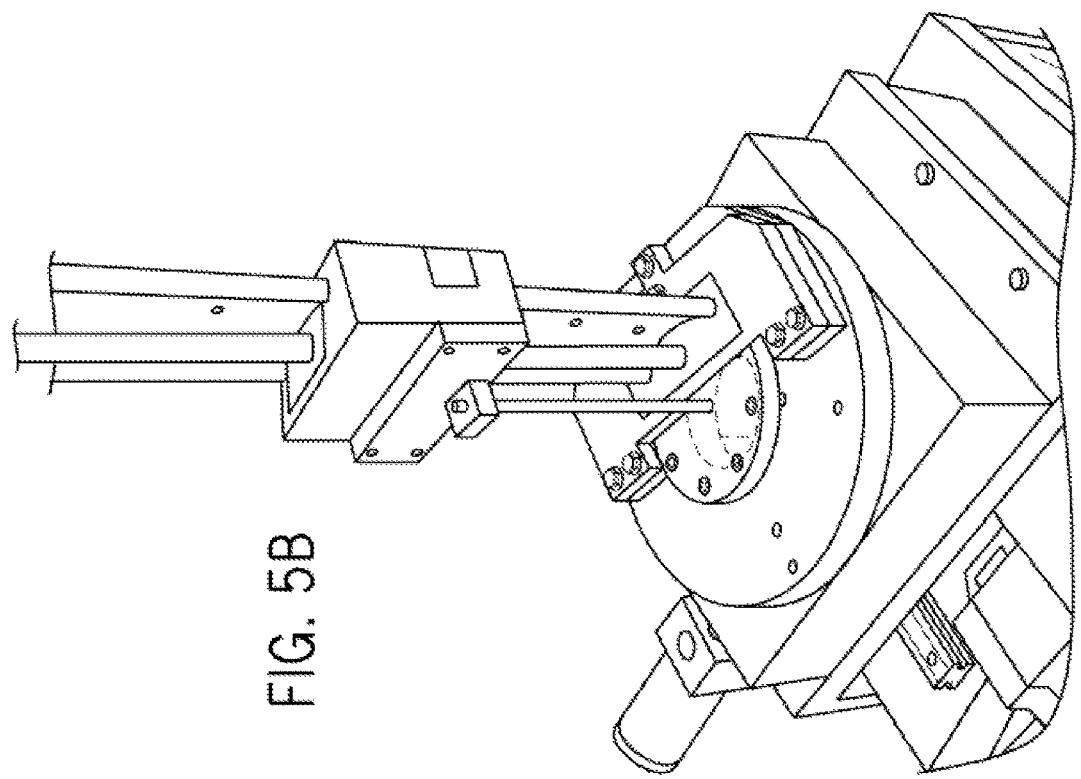
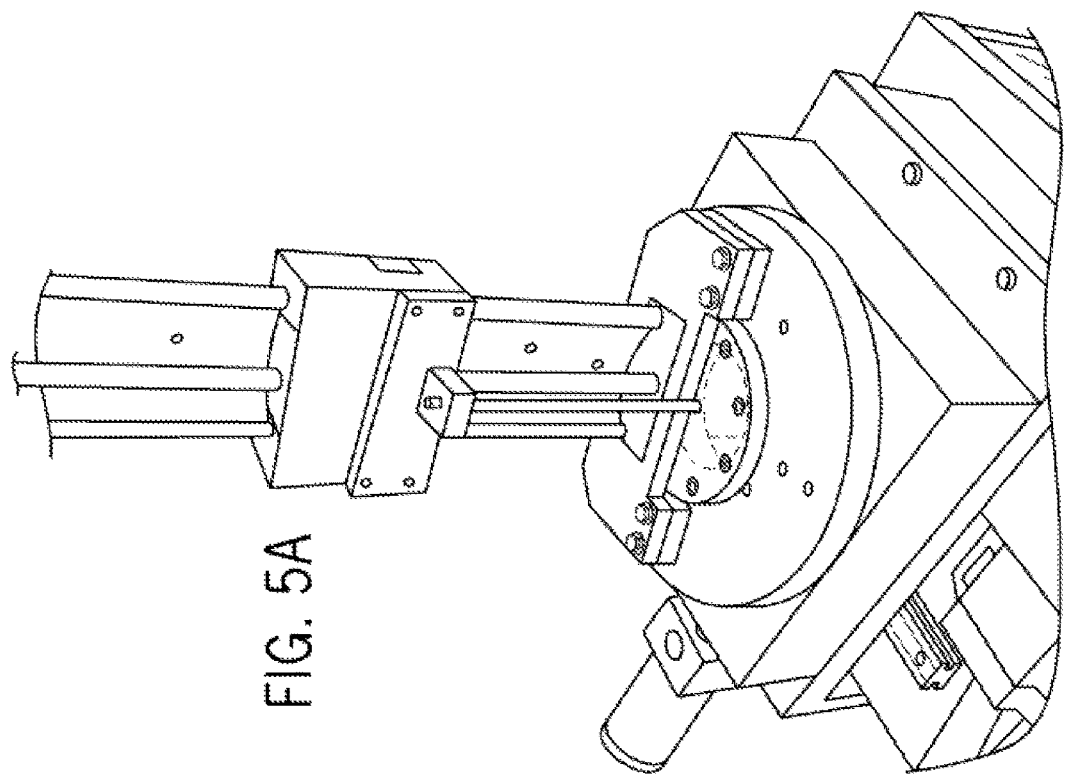
FIG. 5A
FIG. 5B

SURGICAL ROD BENDING SYSTEM AND METHOD

CROSS-REFERENCE

This application is a divisional of U.S. application Ser. No. 14/649,018 filed Jun. 2, 2015, which represents the national stage entry of PCT International Application No. PCT/US2013/070773 filed Nov. 19, 2013, which claims priority to U.S. Provisional Application Ser. No. 61/733,752 filed Dec. 5, 2012, the disclosures of which are incorporated by reference here in their entirety for all purposes.

BACKGROUND OF THE INVENTION

The present application is directed to systems and methods for surgical rod bending. More particularly, the present invention relates to a system and method for controlling a surgical rod bending system to effectuate improved creation of surgical rods.

Surgical rods are used with bone screws in spine surgery to add stability to and/or correct curvatures of the spine. Surgical rods often have to be contoured to fit a desired curve of the spine and to intersect with sometimes irregular locations of bone screw heads.

Currently, the most common method for imparting complex bends to surgical rods is entirely manual. A surgeon must first determine the desired curvature of the rod by temporarily positioning a flexible surrogate rod in the bone screw heads and bending the surrogate rod by hand until it fits properly in each bone screw head. The surgeon must then remove the surrogate from the surgical table and take the surrogate to a side table where it is used as a visual guide to bend an actual surgical rod with a manual rod-bending tool. This procedure is subjective and can lead to metal fatigue if the surgical rod is accidentally over-bent and then re-bent in the opposite direction. In addition, this method can often subject the surgical rod to an increased risk of surface damage caused by accidental contact with sharp metal tools, resulting in local stress riser points and potential rod breakage after implantation. This method is also time-consuming, especially for inexperienced surgeons.

Attempted solutions to the above manual methods involve automated mapping and bending of surgical rods. For example, some newer systems include an input device that receives or calculates virtual coordinates of a surgical rod with a desired curvature, and a motorized rod-bending device that bends a surgical rod according to the coordinates. More specifically, the coordinates are used to produce bend commands for controlling linear and rotational movement of a straight surgical rod as it is fed through the motorized rod-bending device. The bend commands are also used to control a force-actuating mechanism which bends the surgical rod around a post as it is fed through the motorized rod-bending device.

Common force-actuating mechanisms include bending arms which impose a radial or rotating force on the surgical rod so that the surgical rod bends around the post. These force-actuating mechanisms tend to be bulky and require substantially large systems for applying enough force to bend the surgical rods. In addition, some force-actuating mechanisms fail to provide enough support for the surgical rod to ensure that bending only occurs at the desired points. Other force-actuating mechanisms provide such support but, as a result, impose additional limitations such as restricting the degree of rotation of the surgical rod as it is fed through the rod-bending device. These restrictions limit the range of bending capabilities of the rod-bending device and therefore only permit certain combinations of rotation and bending.

Therefore, it would be desirable to provide a compact system to automatically bend a surgical rod to a desired curvature. Furthermore, it would be desirable to have such system sufficiently support the surgical rod without restricting its range of bending capabilities. Further still, it would be desirable to have methods and apparatuses for creating, detecting, and finalizing a desired curvature of a surgical rod using an automatic rod bending system.

SUMMARY OF THE INVENTION

The present invention overcomes the aforementioned drawbacks by providing an automated surgical rod bending system that permits full rotation of a surgical rod as it passes through the system, independent of previous bends performed along the length of the surgical rod. The present invention additionally incorporates methods for detecting a desired curvature of a surgical rod and outputting such detection information to the automated surgical rod bending system. Further still, the present invention provides methods for controlling an automatic rod bending system.

In accordance with one aspect of the invention, a method is disclosed for bending a rod configured to be implanted into a patient. The method includes determining a shape for the rod to be formed into to allow a rod to be implanted into a patient, determining a plurality of pedicle points along the rod where pedicle screws will attach the rod to the patient when the rod is in the shape, and determining a plurality of intermediate points along the rod and between he plurality of pedicle points. The method also includes identifying a plurality of line segments defined by adjacent ones of at least one of the plurality of pedicle points and the plurality of intermediate points and determining an angle measurement to be formed between at least two adjacent ones of the plurality of line segments to form the rod into the shape. The method further includes determining bending parameters to perform on the rod to form the angle measurement between the at least two adjacent ones of the plurality of line segments and feeding the rod into a bending system configured to bend the rod into the shape using at least one of the bending parameters and the angle measurement.

In accordance with another aspect of the invention, a system is disclosed for bending a rod into a shape designed for implantation into a patient. The system includes a plurality of guide rollers, a linear movement device configured to axially feed the rod in a first direction between the plurality of guide rollers, and a rotational movement device configured to rotate the rod as it is axially fed between the plurality of guide rollers. The system also includes a bending device configured to impose bending forces against the rod in a second direction perpendicular to the first direction after it is fed between the plurality of rollers. The bending device is positioned adjacent to the plurality of guide rollers so that the imposed bending forces against the rod causes the rod to bend along a curve of one of the plurality of guide rollers. The system further includes a controller configured to receive an indication of a plurality of line segments defined on the rod and an indication of an angle measurement to be formed between at least two adjacent ones of the plurality of line segments. The controller is further configured to identify bending parameters to perform on the rod to form the angle measurement between the at least two adjacent ones of the plurality of line segments and control operation of at least the bending device using the bending parameters to create an angle having the angle measurement between the at least two adjacent ones of the plurality of line segments.

In accordance with another aspect of the invention, a system is disclosed for bending a rod into a shape designed for implantation into a patient. The system includes a base including a base passage extending there through, a linear movement device configured to axially feed the rod in a first direction through the base passage, and a rotational movement device coupled to one of the base and the linear movement device, the rotational movement device configured to rotate the rod while being fed through the base passage by the linear movement device. The system also includes a bending device moveable in a second direction perpendicular to the first direction to impose bending forces against the rod and a controller. The controller is configured to receive an indication of a plurality of line segments defined on the rod and an indication of an angle measurement to be formed between at least two adjacent ones of the plurality of line segments. The controller is also configured to identify bending parameters to perform on the rod to form the angle measurement between the at least two adjacent ones of the plurality of line segments and control operation of at least the bending device using the bending parameters to create an angle having the angle measurement between the at least two adjacent ones of the plurality of line segments.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIGS. 4A and 4B are a series of perspective views of the system of FIG. 1 in different linear positions.

FIGS. 5A-5C are a series of perspective views of the system of FIG. 1 in different rotational positions.

DETAILED DESCRIPTION OF THE INVENTION

Figure 1:
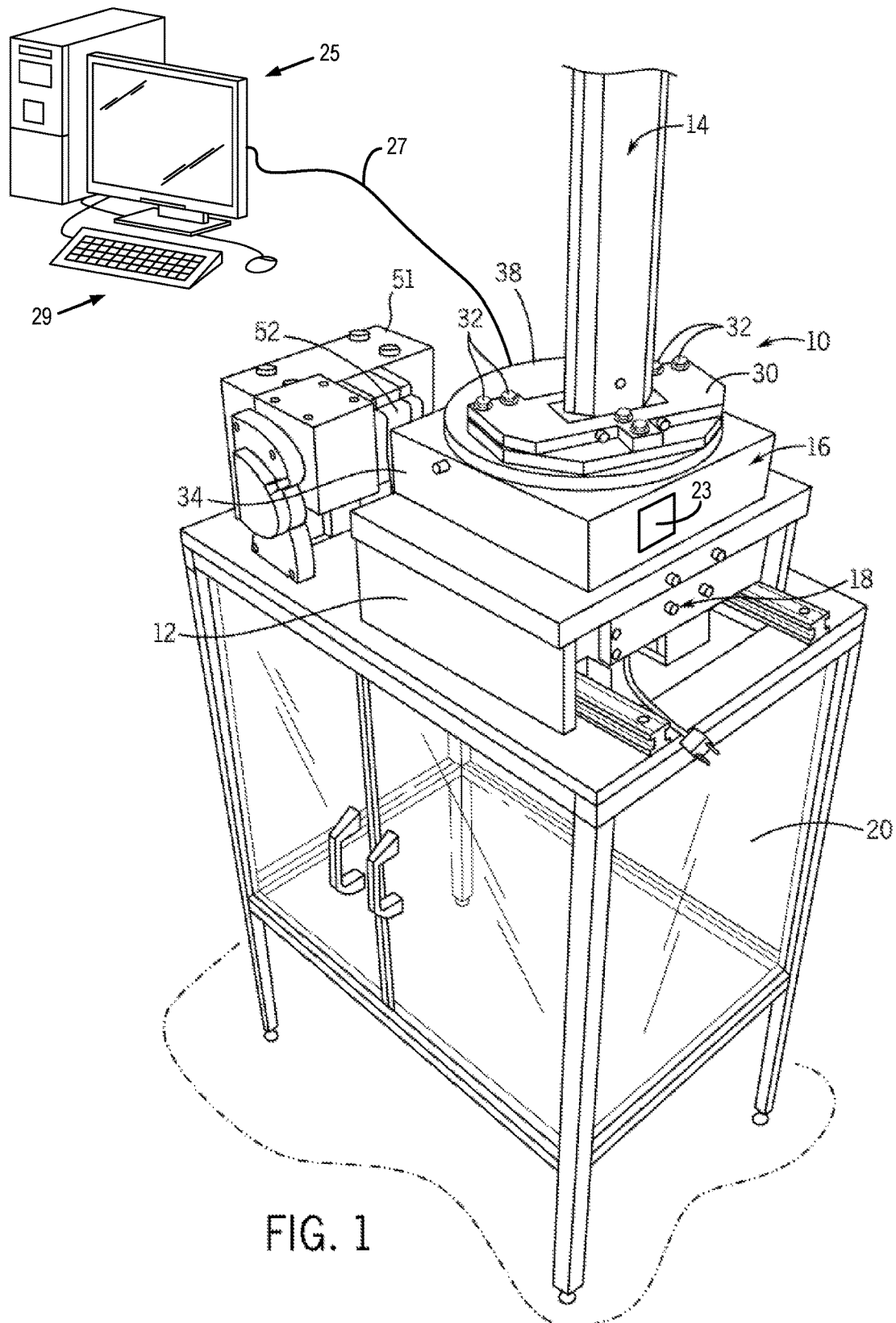
FIG. 1 is a perspective view of an automated surgical rod bending system in accordance with and/or for use with the present invention.

FIG. 1 illustrates an automated surgical rod bending system 10 according to the invention. The system 10 can be used to automatically bend a substantially straight rod to a desired curvature. For example, the system 10 can be used in an operating room to automatically bend an implantable surgical rod for pedicle screw surgery.

Figure 2:
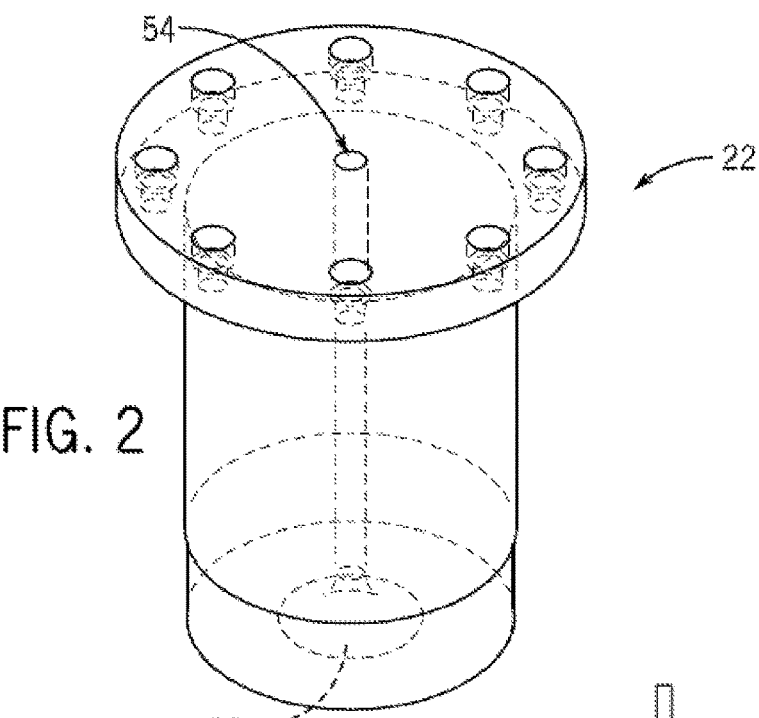
FIGS. 2 and 3 are perspective and cross-sectional schematic views, respectively, of a rod guide for use with the system of FIG. 1.
Figure 3:
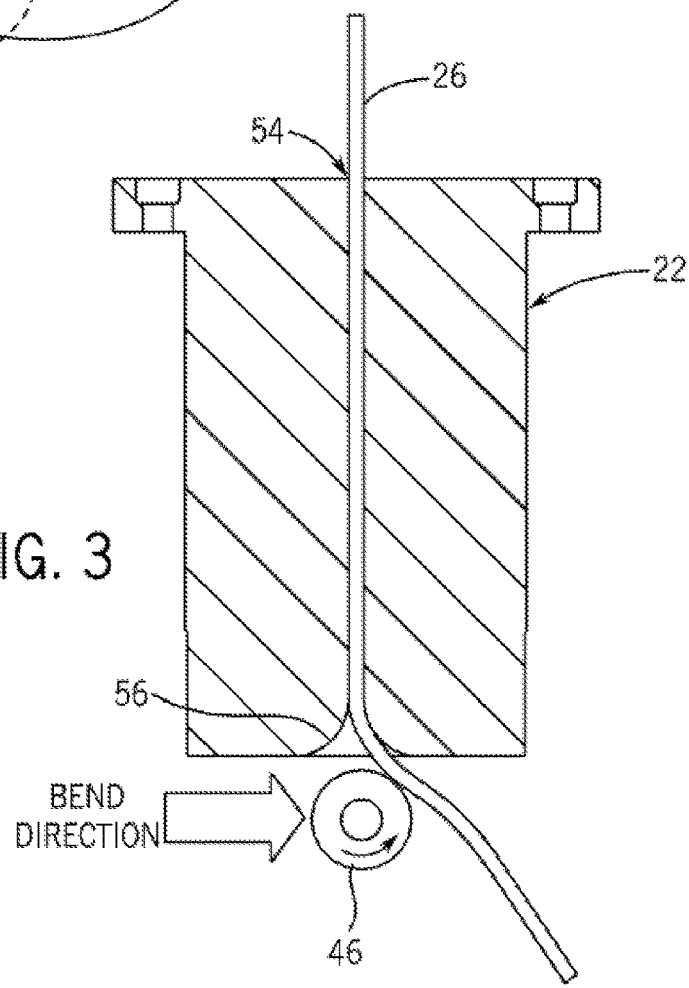

In some embodiments, as shown in FIG. 1, the system 10 can include a base 12, a linear movement device 14, a rotational movement device 16, a bending device 18, a receiving container 20, a rod guide 22 (as shown in FIGS. 2 and 3), and a controller 23. The controller 23, as will be described, can be in communication with and can operate the linear movement device 14, the rotational movement device 16, and/or the bending device 18 (for example, by controlling motors for each device 14, 16, 18, as described below). Additionally or alternatively, a computer system or separate controller 25 may be coupled to the system 10, such as through a cable 27 or wireless connection, to coordinate operation with the controller 23 or to control the system 10 without the controller 23. For example, the computer/controller 25 may include a user interface 29 configured to receive input used to automatically bend a rod. Also, as shown in FIGS. 4A-5C, the system 10 can include a rod holder 24 coupled to the linear movement device 14 for holding a surgical rod 26. As will be described, the bending device 18 may be designed to also achieve cutting of the surgical rod 26 in addition to bending.

Figure 6:
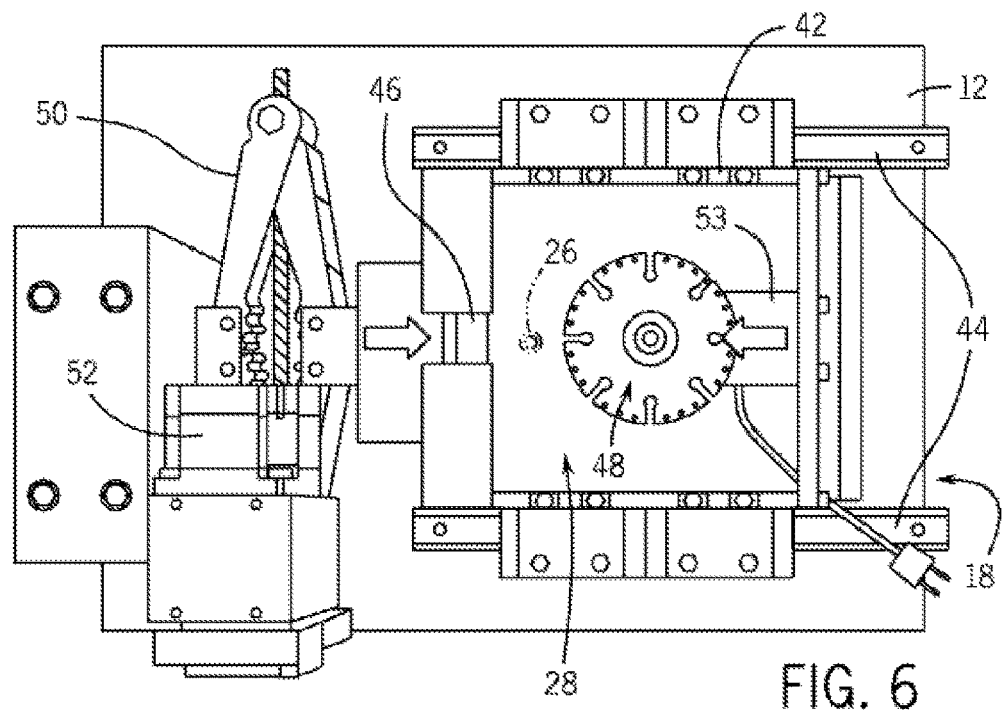
FIG. 6 is a partial top view of the system of FIG. 1.
Figure 7:
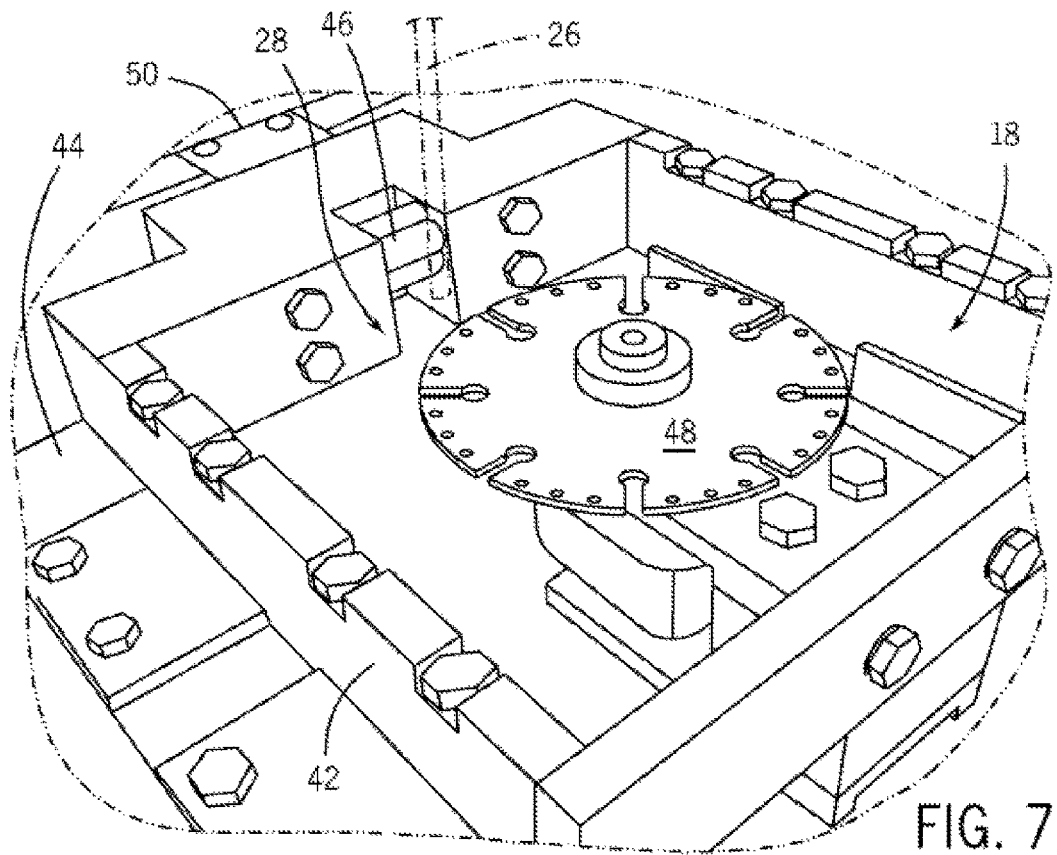
FIG. 7 is a partial perspective view of the system of FIG. 1.

In operation, the system 10 can rigidly hold the trailing end of the surgical rod 26, feed the surgical rod 26 axially through a passage 28 of the base 12 (as best shown in FIGS. 6 and 7), and rotate the surgical rod 26 so that bending can be imposed in a desired direction. More specifically, the surgical rod 26 can be coupled to or secured by the rod holder 24. The controller can operate the linear movement device 14 to vertically feed the surgical rod 26 through the base passage 28 into the receiving container 20. As the surgical rod 26 is fed through the base 12, the bending device 18 can impose bends at different points along the length of the surgical rod 26 and, in some configurations, can cut the surgical rod 26 at a desired length. Further, the rotational movement device 16 can control the rotational orientation of the surgical rod 26 with respect to the bending device 18 as the surgical rod 26 is fed through the base 12.

Figure 5C:
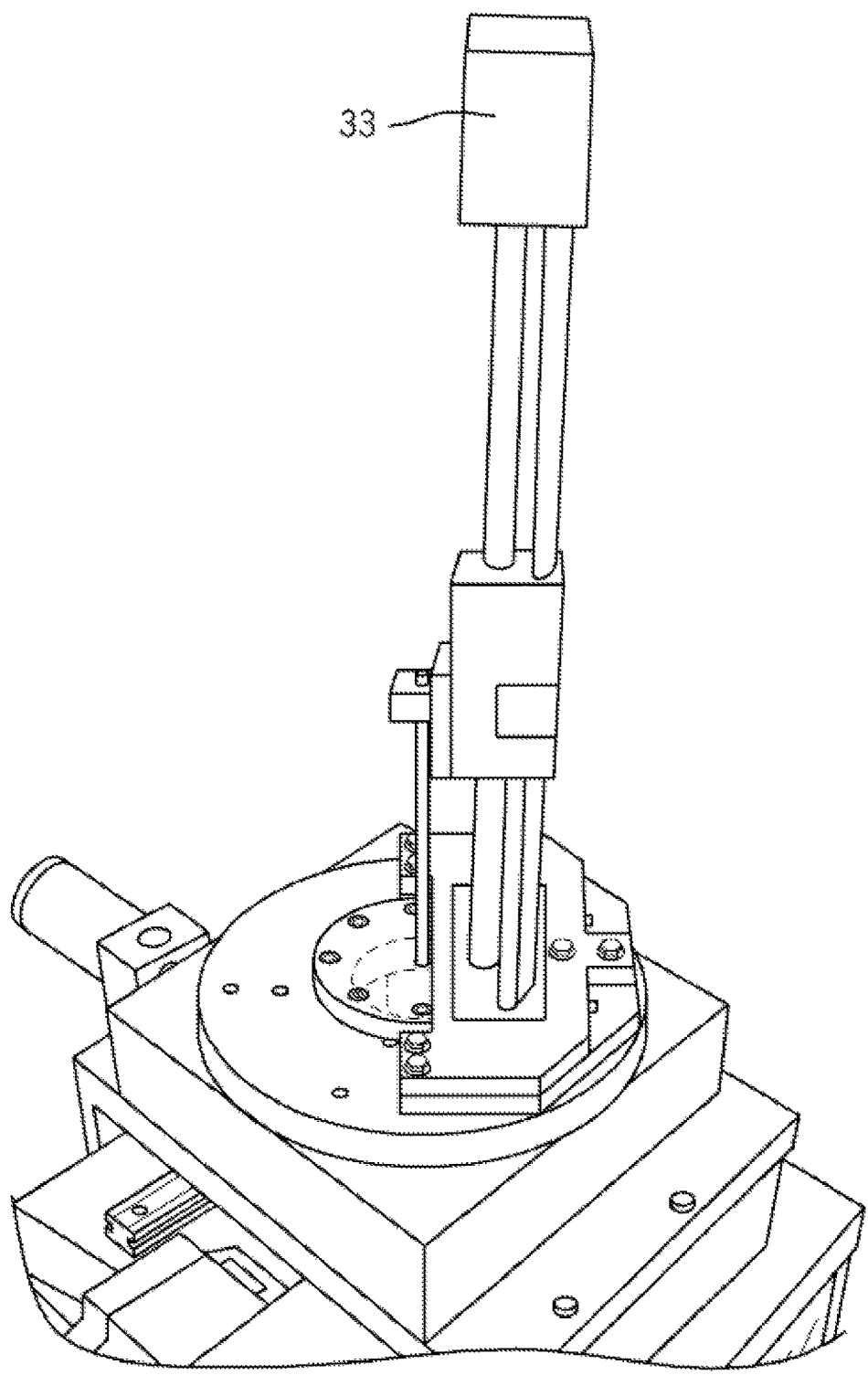

In some embodiments, the linear movement device 14 can be a linear actuator mounted substantially perpendicular to the base 12 and controlled by a first stepper motor 33, as shown in FIG. 5C. The linear movement device 14 can be positioned so that its movement axis is substantially vertical. For example, FIGS. 4A and 4B show the linear movement device 14 in a first position and a second, vertically lower position, respectively. The first stepper motor 33 can control the linear movement device 14 to feed the surgical rod 26 vertically down through the base passage 28 at programmed length increments. In one embodiment, as shown in FIG. 1, the linear movement device 14 can be coupled to the rotational movement device 16 by a coupling mechanism 30 and fasteners 32.

In some embodiments, the rotational movement device 16 can include a rotational actuator 34 mounted substantially parallel to the base 12 and controlled by a second stepper motor 36, as shown in FIGS. 4A-4B. The rotational movement device 16 can also include a rotatable platform 38 coupled to the rotational actuator 34, for example via a rotational bearing (not shown) embedded in the platform 38. The platform 38 can also include a platform passage (not shown) aligned with the base passage 28. The linear movement device 14 can be coupled to the platform 38, as described above, allowing the rotational movement device 16 to control the radial orientation of the linear movement device 14, and thus, the surgical rod 26 with respect to the bending device 18. The second stepper motor 36 can operate the rotational movement device 16 to rotate in one or both directions (that is, positive or negative rotation) between zero degrees and about 360 degrees in programmed increments. For example, FIG. 5A shows the rotational movement device 16 in a first position, FIG. 5B shows the rotational movement device 16 in a second position rotated from the first position by a first degree amount, and FIG. 5C shows the rotational movement device 16 in a third position further rotated from the first position by a second, larger degree amount. In one embodiment, the rotational movement device 16 can be controlled to rotate in increments of about 0.005 degrees.

In some embodiments, the rod guide 22 can be coupled to the platform 38 so that it extends through the platform passage and terminates adjacent to the bending device 18 and/or the base passage 28. As shown in FIGS. 2 and 3, the rod guide 22 can be substantially cylindrical and can include a rod passage 54 for receiving and guiding the surgical rod 26 as it is fed vertically through the platform passage. Bending can be imposed on the surgical rod 26 by the bending device 18 as it exits the rod guide 22.

In some embodiments, the rod passage 54 can terminate with a flared base 56. More specifically, one end of the rod passage 54 (that is, the end adjacent to the base passage 28) can extend radially outward so as to form a outwardly tapering surface that forms a substantial flare outward, as shown in FIGS. 2 and 3. As illustrated, this flared base 56 may advantageously be formed to present a convex surface against which the surgical rod 26 can bend or curve as bending forces are applied by a bending roller 46, as further described below. Other geometries are may be used; however, the flared or convex surface provides an advantageous geometry against which to bend the surgical rod 26 without incurring sharp bends that, for example, may present an unfavorable discontinuous bend (such as those created if the rod is bent too sharply) and/or structural weakness. The cylindrical portion of the rod passage 54 can provide substantial support for the surgical rod 26 to prevent bending or increased stress at other points along the length of the surgical rod 26 as it is bent by the roller 46 and the flared base 56. In one embodiment, the rod guide 22 can rotate with the platform 38 and with the surgical rod 26, allowing bending of the surgical rod 26 to occur against any surface segment of the flared base 56. In another embodiment, the rod guide 22 can remain stationary, allowing the surgical rod 26 to rotate within the rod passage 54 so that bending can occur against the same surface segment of the base 56. In this case, the geometry of the base 56 can be made such that it is only convex on the side against which bending force from the bending device is applied. In addition, in some embodiments, the rod guide 22 can be manufactured from stainless steel or a similar material.

In some embodiments, as shown in FIGS. 6 and 7, the bending device 18 can be coupled to the base 12 and can include a trolley 42 moveable along linear slides 44, a roller 46 coupled to the trolley 42, a cutting wheel 48 coupled to the trolley 42, a scissors jack 50 coupled to the trolley 42, and a third stepper motor 52. The scissors jack 50 allows the bending device 18 to exert large linear forces with a low torque requirement of a driving motor. Other mechanisms for creating linear forces can be used, such as screw drive mechanisms or electromagnetic, hydraulic, or pneumatic piston actuators. The third stepper motor 52 can be operated in forward and reverse to move the scissors jack 50 between a retracted position (as shown in FIG. 6) and an extended position. Extension and retraction of the scissors jack 50 can cause the trolley 42 to traverse across the base passage 28 in a first horizontal direction (for example, away from the third stepper motor 52) and a second horizontal direction (for example, toward the third stepper motor 52). As the surgical rod 26 is vertically fed through the base passage 28, movement of the trolley 42 in the first horizontal direction can allow the roller 46 (for example, a roller bearing) to contact the surgical rod 26, causing the surgical rod 26 to bend. In addition, movement of the trolley 42 in the second direction can allow the cutting wheel 48 to contact and cut the surgical rod 26. In some embodiments, as shown in FIG. 1, the system 10 can include a block 31 or similar stability component coupled to the base 12 and one side of the scissors jack 50 (i.e., the side opposite the trolley 42) can be coupled to the block 51. The block 51 can provide a non-moving part for the scissors jack 50 to press against so that retraction and extension of the scissors jack 50 causes linear movement of the trolley 42.

The third stepper motor 52 and the scissors jack 50 can provide sufficient force to allow the roller 46 to exert bending forces against the surgical rod 26. The increment of distance of travel of the linear movement device 14 and the distance of travel of the bending device 18 toward the surgical rod 26 can affect the type of bend that results. For example, a gentle bend can be imposed by feeding the surgical rod 26 in small increments by advancing the linear movement device 14 and applying minimal displacement of the bending device 18 at each increment, or a sharper bend can be imposed by applying a large displacement of the bending device 18 without incrementing the linear movement device 14, forcing the surgical rod 26 to conform to the flared base 56. In one embodiment, a minimal possible bend curvature imposed on the surgical rod 26 can be dependent on the curvature of the flared base 56. As the name implies, the roller 46 can roll in order to minimize shear forces against the surgical rod 26 as it is bent against the flared base 56.

In addition, in some embodiments, the cutting wheel 48 can be diamond-tipped and/or can be rotatable (for example, by a motor 53, as shown in FIG. 6, connected to an external power source) to permit a substantially clean cut across the surgical rod 26. In other embodiments, the cutting wheel 48 can be substituted with pliers, guillotine, or other mechanical or electrical cutting devices. In some embodiments, components of the linear movement device 14, the rotational movement device 16, and/or the bending device 18 can be manufactured from aluminum and/or stainless steel.

In other embodiments, the base 12 can comprise a different orientation relative to the linear movement device 14, the rotational movement device 16, and/or the bending device 18. For example, the bending device 18 can have a supporting base mechanism that allows it to be oriented at any angle in the plane of the base 12 relative to the platform passage of the bending device 18, thereby allowing bending to occur in more than one direction. In addition, in some embodiments, the bending device 18 may only include components for bending the surgical rod 26, while a separate, independent device includes components for cutting the surgical rod 26, and vice versa.

In conventional rod benders, previous bends may prevent a surgical rod from being rotated in a certain direction to impose subsequent bends. This limitation is often due to such conventional rod benders requiring rod guides that extend past the bending device, or requiring the bend to occur while the rod rests flat against a planar surface. In some embodiments, due to the relative orientation of the linear movement device 14, the rotational movement device 16, the rod guide 22, and the bending device 18, the system 10 may be free of barriers or other components contacting the surgical rod 26 after it passes across the bending device 18 (that is, after it is fed past the roller 46). In addition, the receiving container 20 can be substantially large enough to allow free movement of the surgical rod 26 as it is fed through the base 12 until it is cut by the bending device 18. As a result, the system 10 can allow unlimited rotation of the surgical rod 26 in either direction for subsequent bending, independent of the previous bends made. In addition, in comparison to manual rod bending, the system 10 can produce an accurately bent surgical rod 26 in minimal time.

In some embodiments, the controller can control each of the stepper motors 33 (causing linear actuation), 36 (causing rotation actuation), 52 (causing bending device actuation). In other embodiments, each of the stepper motors 33, 36, 52 can be controlled by individual controllers. Each stepper motor 33, 36, 52 can be pre-programmed to perform its respective movement operations in predetermined increments. For example, the third stepper motor 52 can control movement of the scissors jack 50 in predetermined increments in order to achieve a desired bend. Also, one or more of the stepper motors 33, 36, 52 can be programmed to operate additional components of the system 10. In one embodiment, the controller can control a relay that powers the motor 53 for rotation of the cutting wheel 48. In another embodiment, a switch can be activated to power the cutting wheel motor 53 when the trolley 48 of the bending device 18 crosses an optical sensor or touch sensor (for example, as it moves the cutting wheel 48 in proximity to the surgical rod 26).

In some embodiments, a shield or housing (not shown) can enclose some or all of the components of the system 10. For example, in one embodiment, a protective shield can substantially block access to the bending device 18 during operation of the system 10. In addition, in some embodiments, the system 10 can include a sterilization mechanism (e.g., an autoclave or another suitable sterilization mechanism) to sterilize the surgical rod 26 and/or remove metal debris at the cut locations of the surgical rod 26 after it has passed across the bending device 18.

Figure 8:
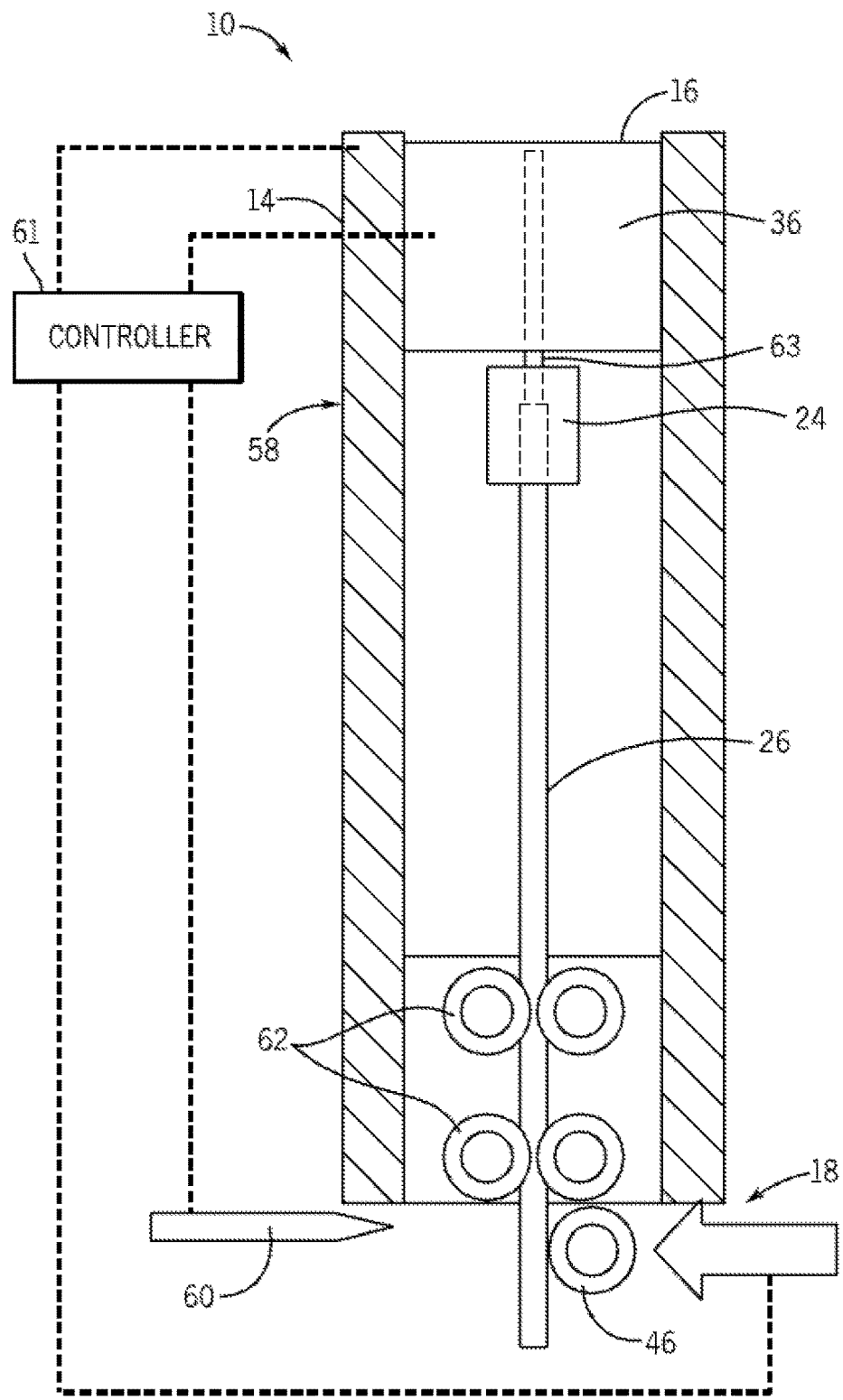
FIG. 8 is a schematic view of an automated surgical rod bending system in accordance with and/or for use with the present invention.

FIG. 8 illustrates the system 10 according to another embodiment of the invention. As shown in FIG. 8, the system 10 can include the linear movement device 14 with linear bearings 58, the rotational movement device 16 including the second stepper motor 36, the rod holder 24, and the bending device or actuator 18 including the bending roller 46 and a cutting blade 60, and a controller 61 (for example, similar to the controller described above with respect to FIGS. 1-7). The system 10 can also include guide rollers 62 that help guide the surgical rod 26 as well as provide a convex surface against which the rod 26 can bend when horizontal force is applied by the bending roller 46.

In the embodiment shown in FIG. 8, the linear movement device 14 can remain stationary, but move the rotational movement device 16 in a linear manner for vertically feed the surgical rod 26 past the bending roller 46. The rotational movement device 16 can cause rotation of the rod holder 24 (for example, via a rotating shaft 63 coupled to the rod holder 24) in order to rotate the surgical rod 26 as it is vertically fed past the bending roller 46. In addition, the horizontal bending forces imposed by the roller 46 against the surgical rod 26 can cause the surgical rod 26 to bend along a curve of one of the guide rollers 62. Once a desired length of the surgical rod 26 has been fed past the roller 46, the cutting blade 60 can be triggered to cut the surgical rod 26.

In some embodiments, the system 10 can be interfaced with an apparatus (not shown) that detects or calculates the desired curvature of a surgical rod and outputs bending commands to the controller 61 of the system 10. The controller 61 can manipulate the position and rotation of the straight surgical rod 26 as it is passed through the system 10 and the amount of travel of the bending roller 46 based on the bending commands.

Figure 9:
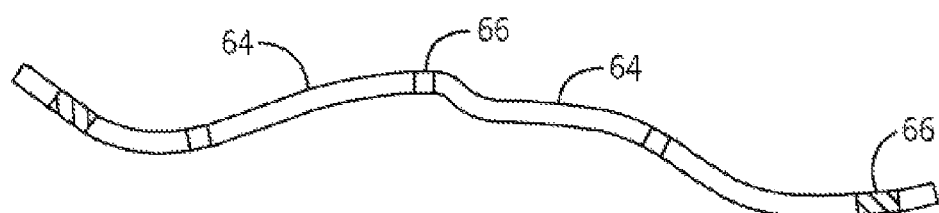
FIG. 9 is a schematic view of a surrogate rod for use with the present invention.
Figure 10A:
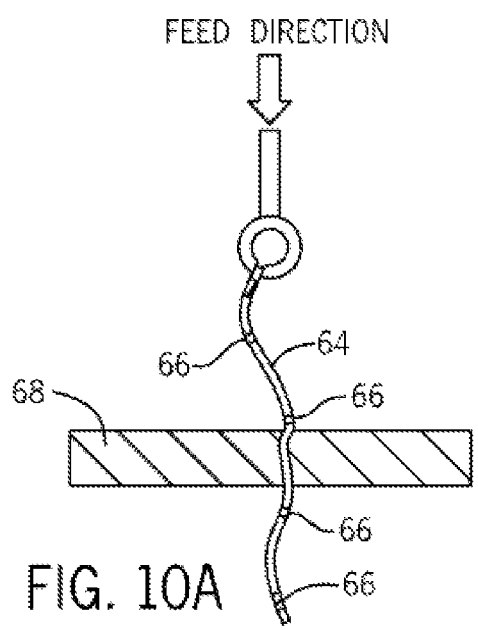
FIGS. 10A and 10B are schematic side and top views, respectively, of a surrogate rod and an optical scanner for use with the present invention.
Figure 10B:
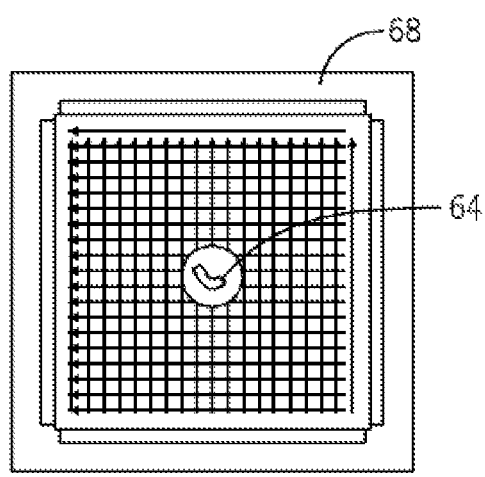

The apparatus can apply one or more methods for determining or detecting a desired surgical rod curvature. For example, a first method can include optical digitization of a surrogate rod 64, as shown in FIGS. 9-10B. The surrogate rod 64 can have mechanical properties similar to a piece of heavy electrical wire and can be bent by a surgeon by hand (that is, without tools) to align with pedicle screws implanted in a patient. Indicators 66, such as clips or markers, can be applied to the surrogate rod 64 to identify desired termini of the rod, screw head locations, possible bone collision points, etc., as shown in FIG. 9. An optical scanner 68 can then be used to scan the surrogate rod 64 and transmit optical scan information to the apparatus. In one embodiment, the surrogate rod 64 can be fed across the optical scanner 68 at a fixed rate, as shown in FIGS. 10A and 10B. The optical scanner 68 can detect rod angles in two planes, or "x" and "y" location coordinates, along an array of linear "z" positions to provide a three-dimensional optical scan.

The apparatus can analyze the scan information, digitally map a three-dimensional model of the surrogate rod 64, and calculate a proposed curvature of the surgical rod 26 (for example, by applying a mathematical spline fit to the three-dimensional model). The apparatus can then transmit bend commands to the system 10 based on the proposed curvature. Other commands can be determined based on the locations of the indicators. For example, the apparatus can output cutting commands where terminus indicators 66 were located on the surrogate rod 64. The apparatus can also minimize bending of the surgical rod 26 where screw head indicators 66 or possible bone collision indicators 66 were located on the surrogate rod 64. Elimination of bends at these points can permit easier insertion of the surgical rod 26 into the slots in the pedicle screw heads after the rod 26 has been bent.

Figure 11:
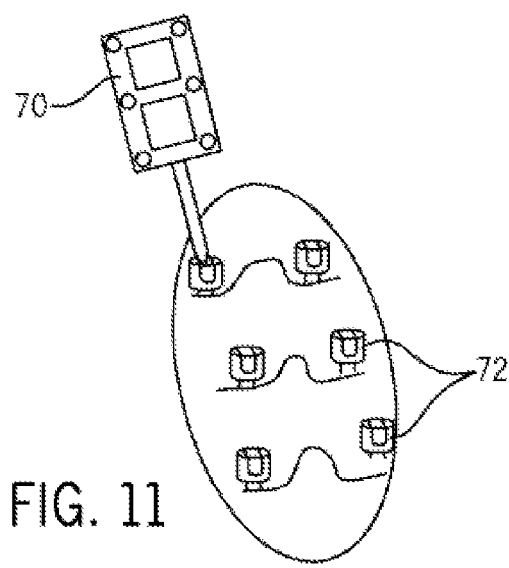
FIG. 11 is a schematic view of a digitizing probe for use with the present invention.

A second method for defining surgical rod curvature can include a digitizing probe 70, as shown in FIG. 11, and an optical system (such as OptoTrak Certus® system or a similar system) to determine key points along a patient's spine during surgery. A surgeon can use the digitizing probe 70 to identify key points, such as screw heads 72, desired termini of the surgical rod, and/or bony structures that might interfere with the surgical rod, as shown in FIG. 11. Markers on the digitizing probe 70 can allow the optical tracking system to accurately track the location of the probe tip as the surgeon identifies the key points. The apparatus can apply a mathematical spline fit (or another suitable curve fit) to define the desired curvature of the surgical rod based on the key points identified and transmit bend commands to the system 10 based on the defined curvature.

As described above, once curvature is defined using the optical scanning method, the digitization method, or another suitable method, the desired rod curvature can be used to create bend commands for the system 10. The apparatus and/or the controller 61 can make adjustments to the desired rod curvature to minimize bone collisions, bending at screw head locations, binding in the guide tube 54 due to bends by the system 10 that are too sharp, and/or other potential issues. These adjustments can minimize the stresses that surgical rods may experience after they are implanted.

The following paragraphs describe methods of using the system 10 for automatically creating bends in a surgical rod 26, in accordance with the present invention. As described above, the system 10 of the present invention is able to create complex bends in more than one plane. However, it is possible to conceptualize the three-dimensional (3D) bending to a two-dimensional (2D) problem to better understand the issues involved. As such, the following example will be described and illustrated in 2D, but can be extended to 3D.

Figure 12:
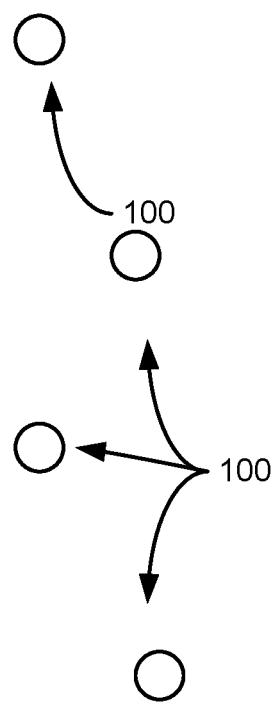
FIG. 12 is a schematic illustration of a plurality of pedicle screw locations determined in accordance with the present invention.
Figure 13:
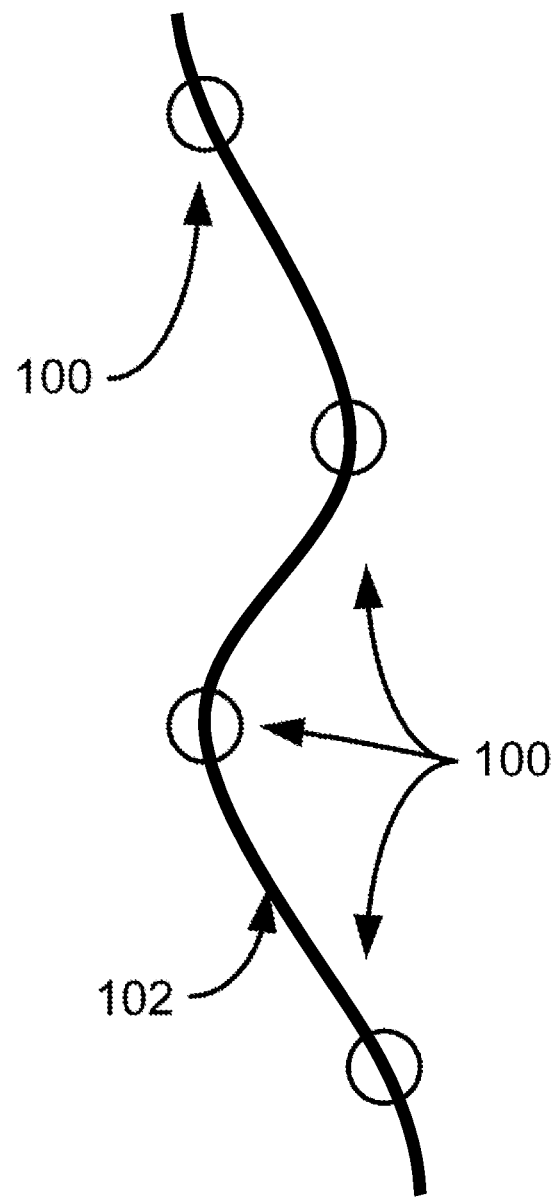
FIG. 13 is a schematic illustration of the plurality of pedicle screw locations of FIG. 12 and a hypothetical rod shape coupled thereto in accordance with the present invention.
Figure 14:
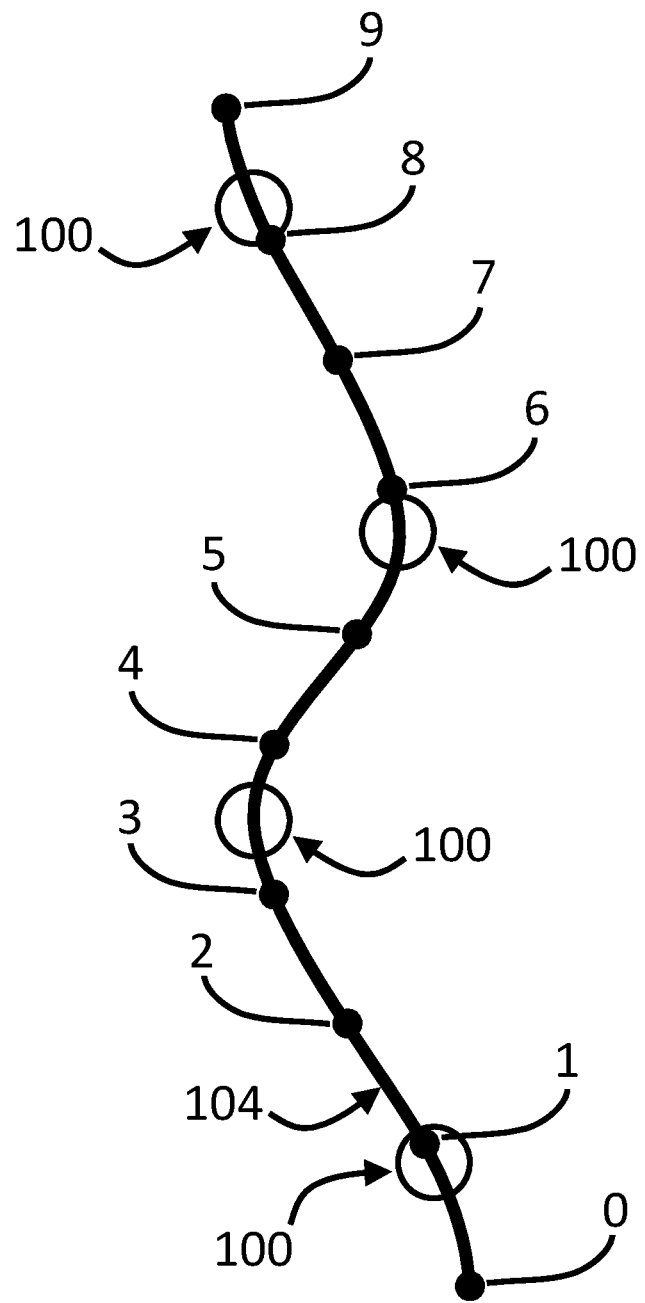
FIG. 14 is a schematic illustration of the plurality of pedicle screw locations of FIG. 12 and the hypothetical rod shape of FIG. 13 coupled thereto and a plurality of intermediate points selected in accordance with the present invention.

FIG. 12 illustrates an example of a 2D bending problem. A series of pedicle screw heads 100 are shown. In FIG. 13, the series of pedicle screw heads 100 are illustrated as dictating the desired path of a hypothetical interconnecting rod 102, which can be automatically bent by the above-described system. Referring to FIG. 14, a spline fit 104 can be used to interconnect these screw heads 100 in a smooth, gentle curve. To do so, a plurality of points 0-9 are distributed along the spline 104. In this example, ten points 0-9 are identified along the spline path 104. As will be described, these points 0-9 can be used as the targets to which each bend aims to fit.

Figure 15A:
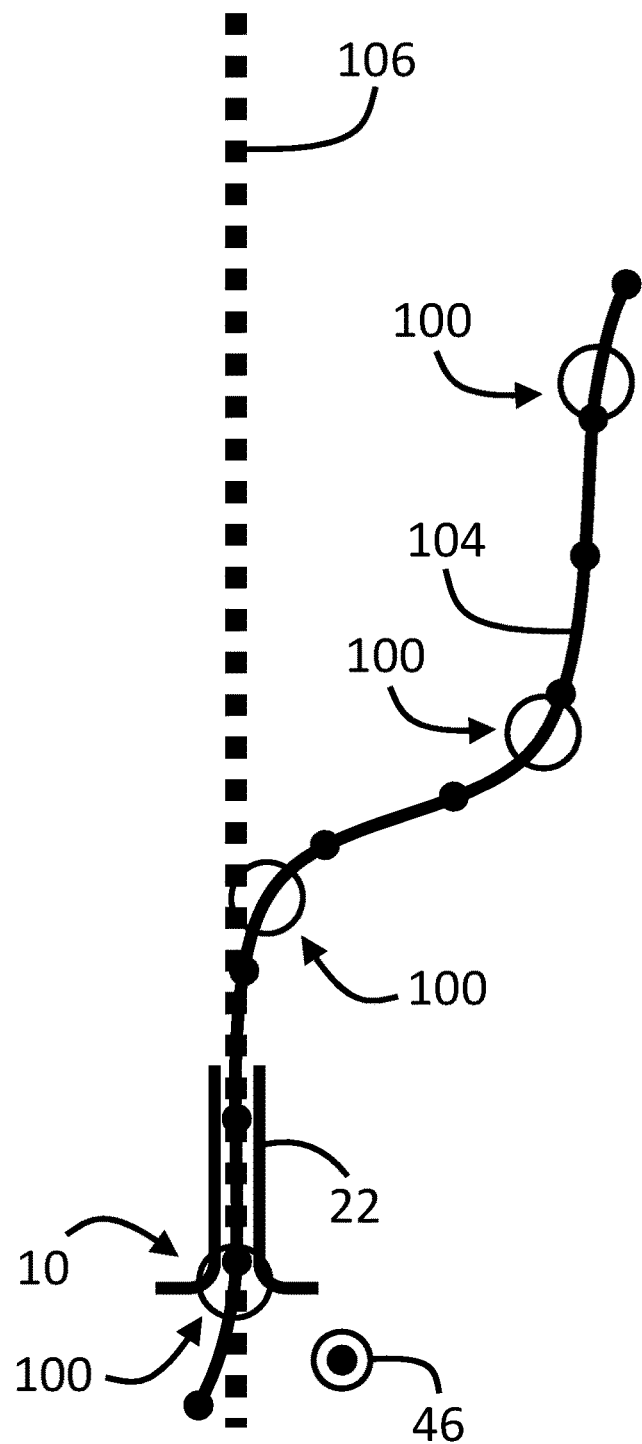
FIGS. 15A through 15P are schematic diagrams illustrating a two-dimensional sequential bending process of a rod using the plurality of pedicle screw locations of FIG. 12, the hypothetical rod shape of FIG. 13 coupled thereto, and the plurality of intermediate points selected in FIG. 14.
Figure 15B:
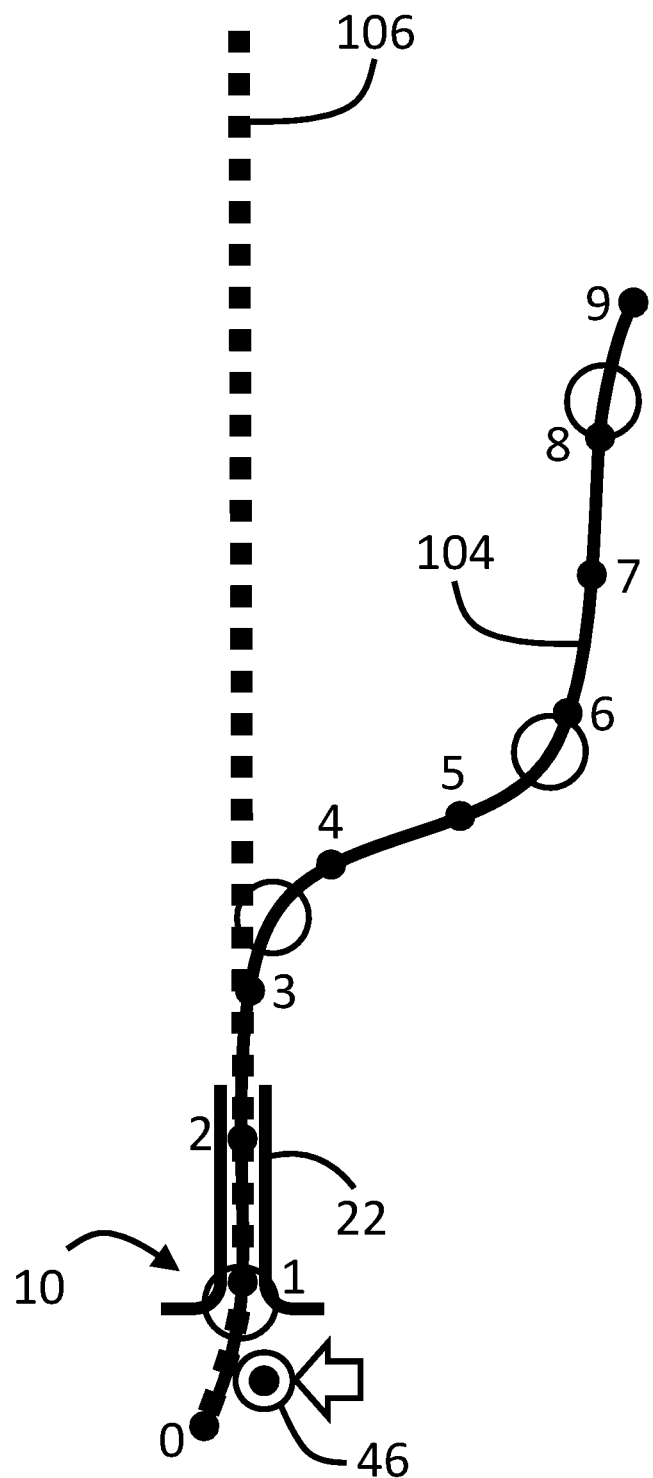
Figure 15C:
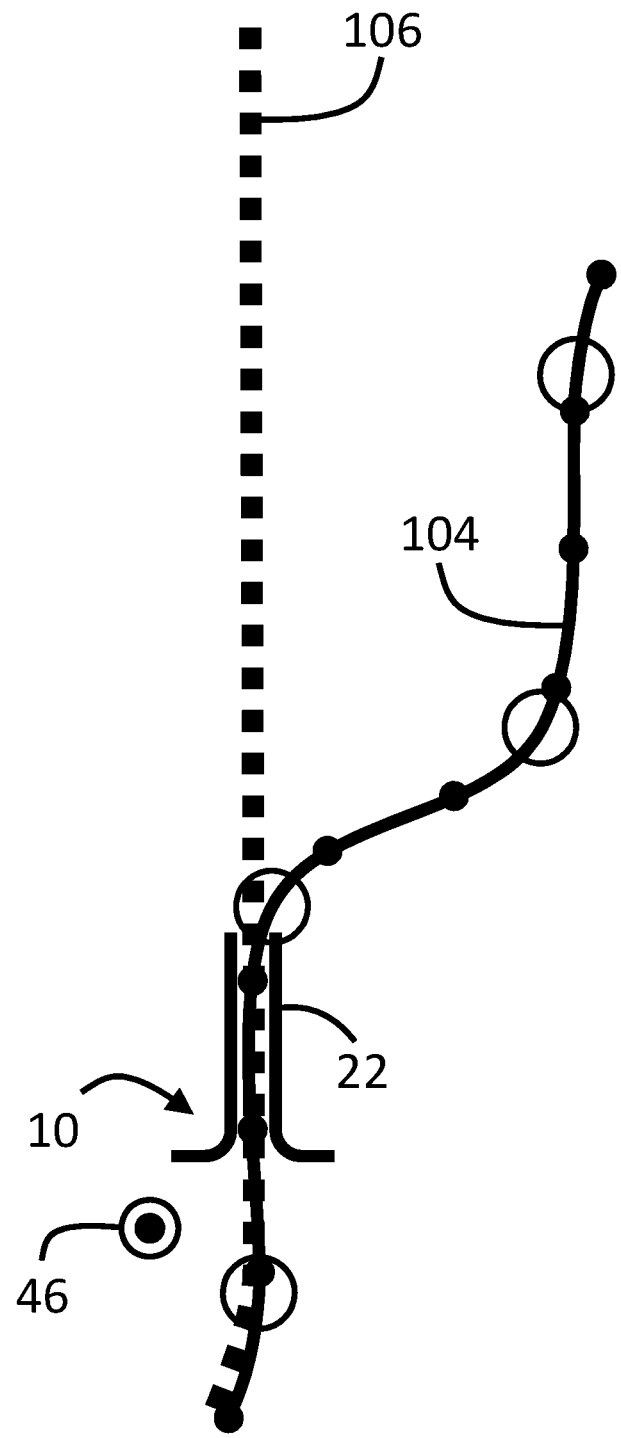
Figure 15D:
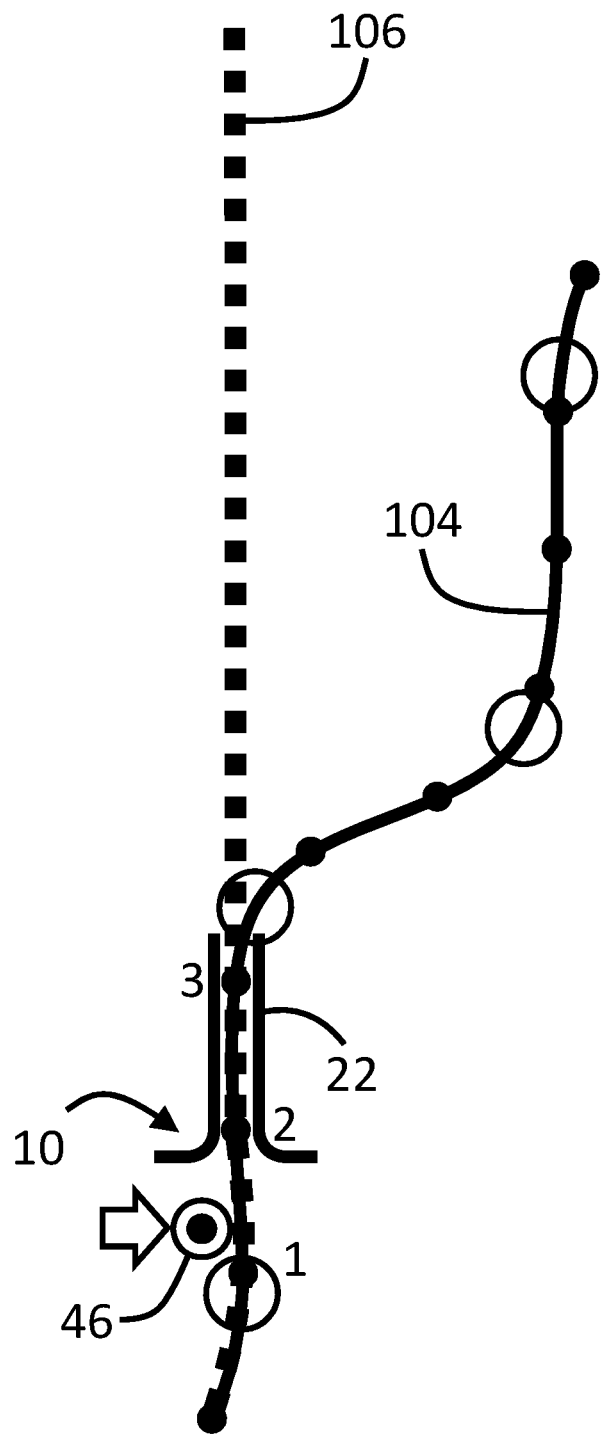
Figure 15E:
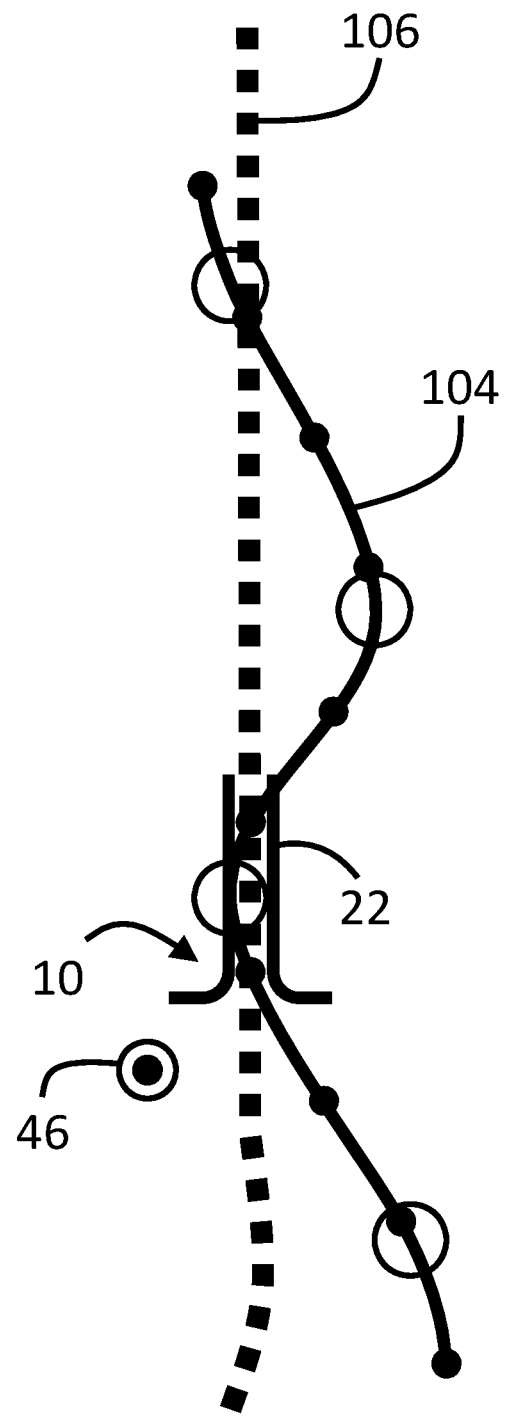
Figure 15F:
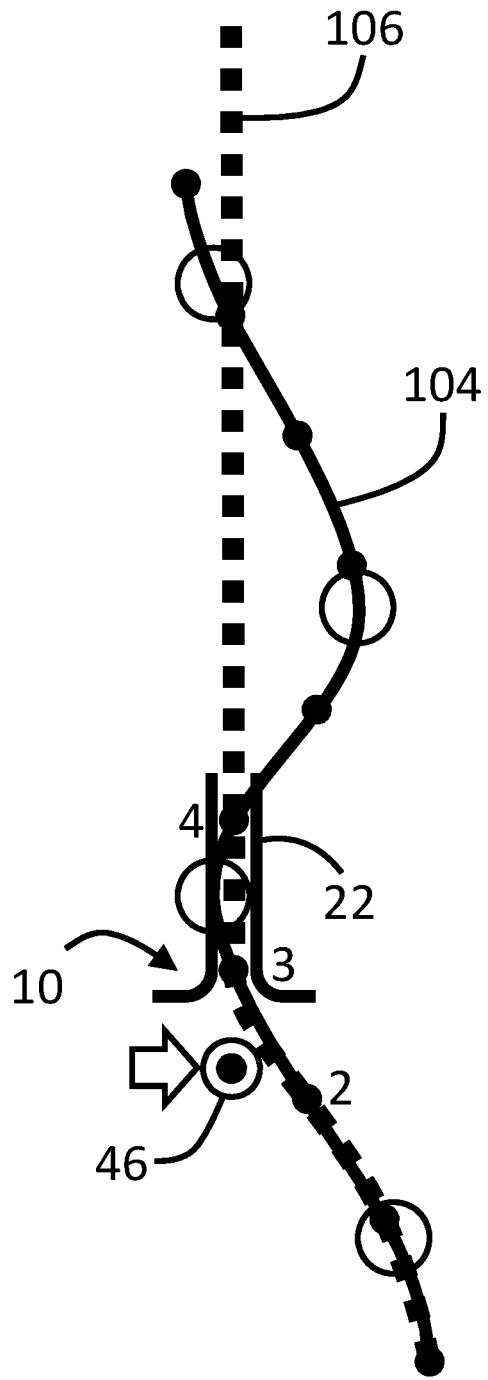
Figure 15G:
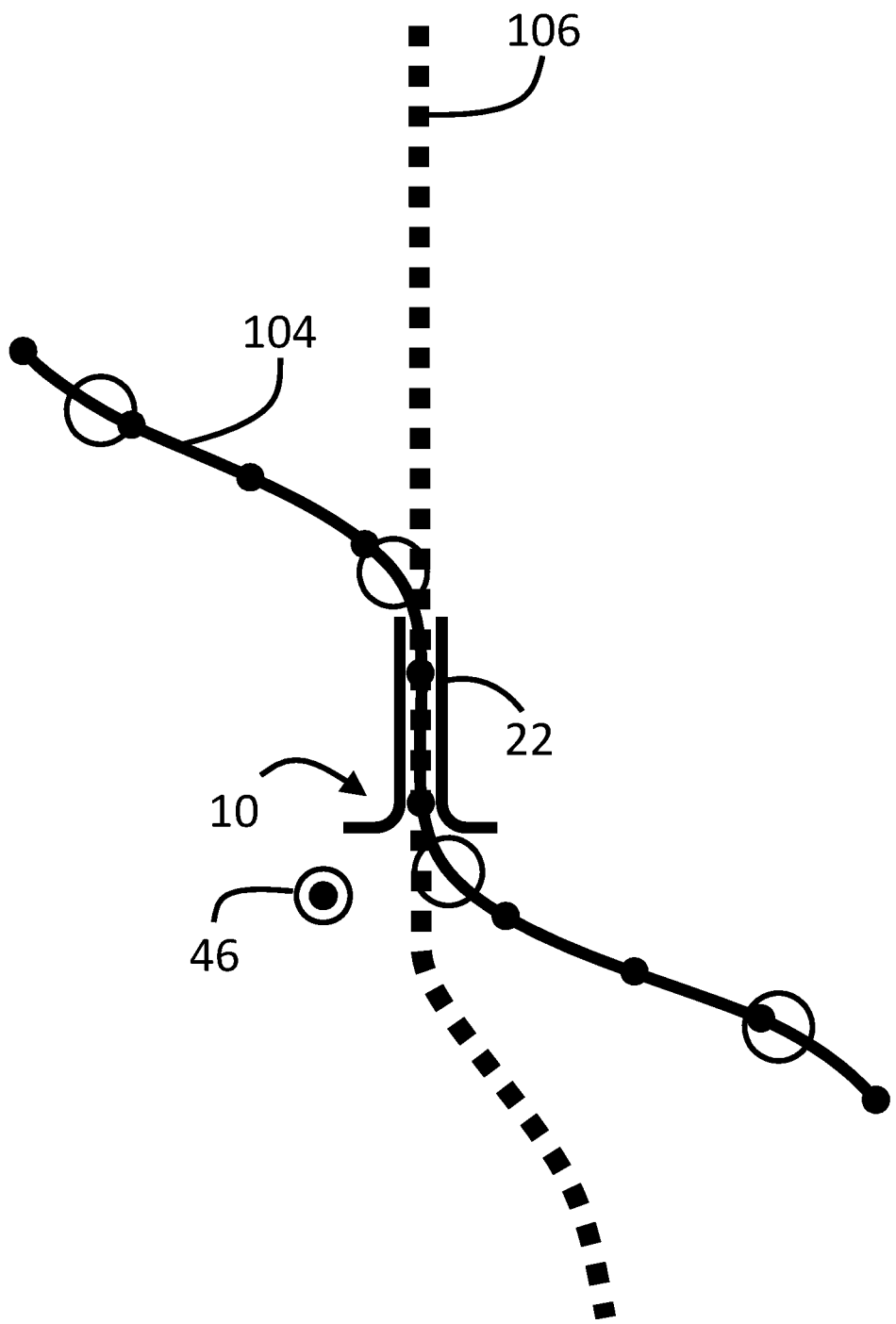
Figure 15H:
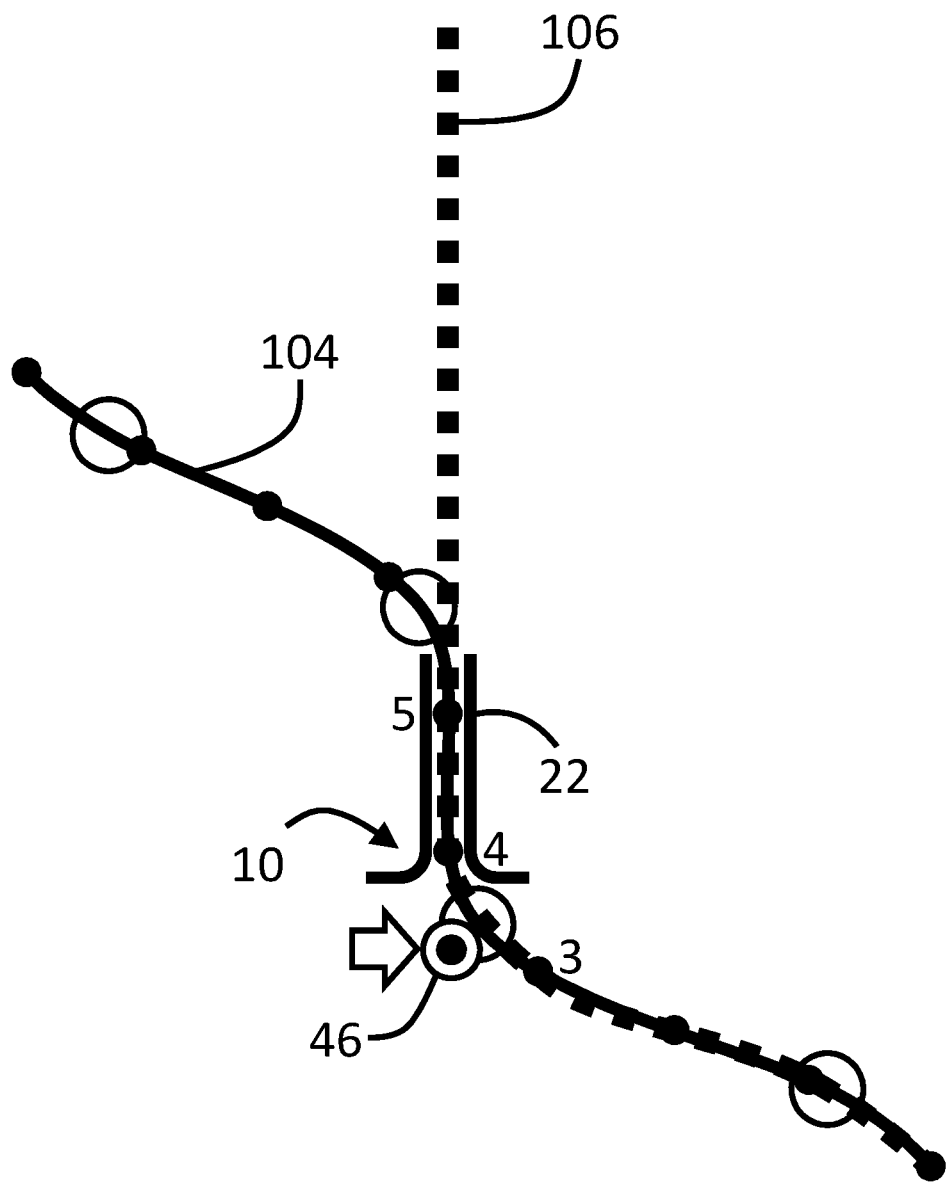
Figure 15I:
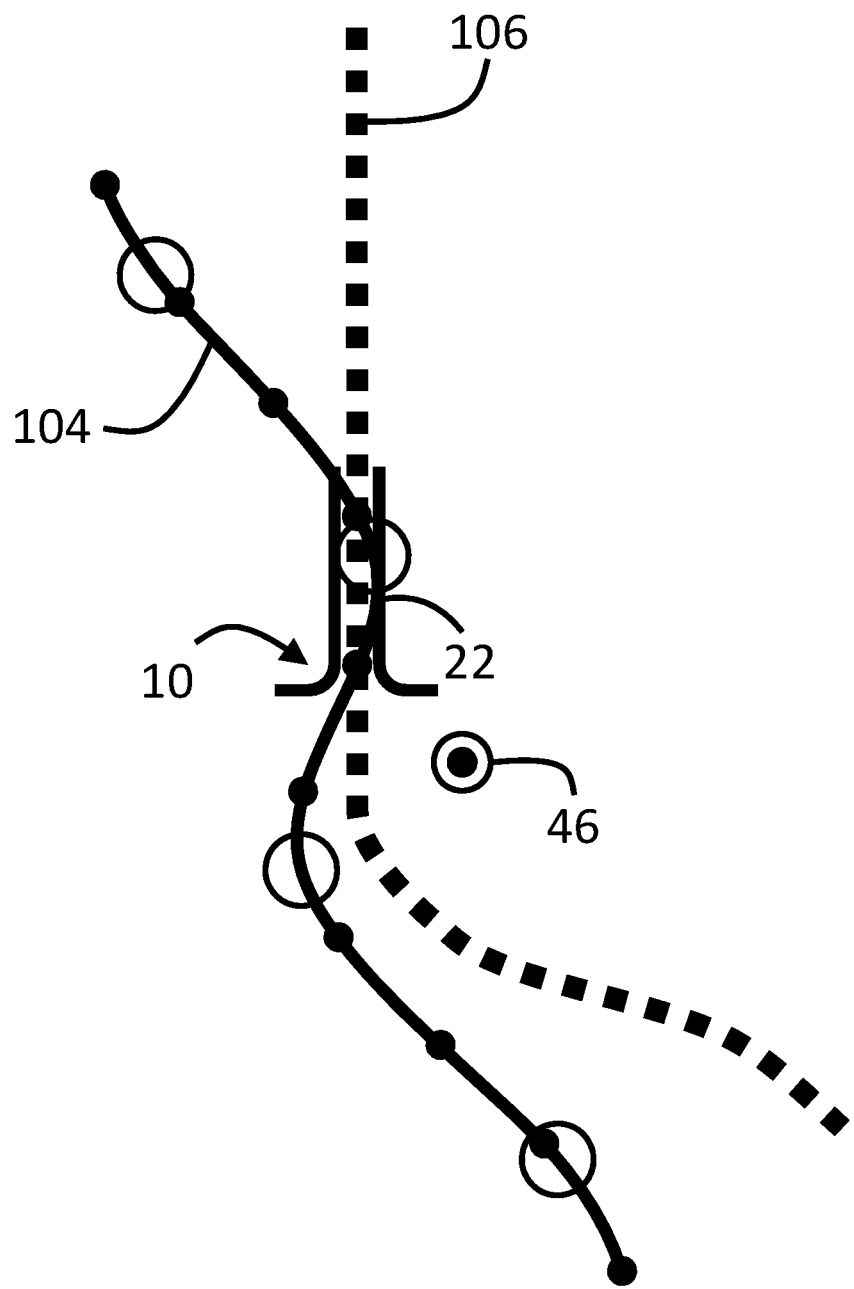
Figure 15J:
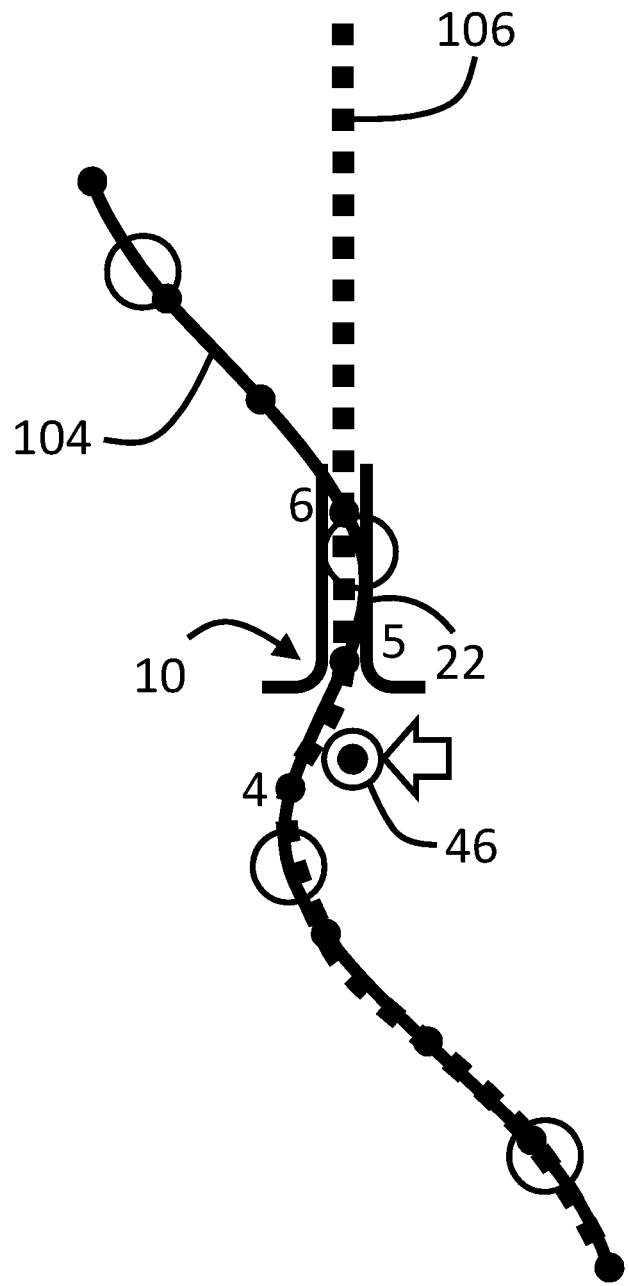
Figure 15K:
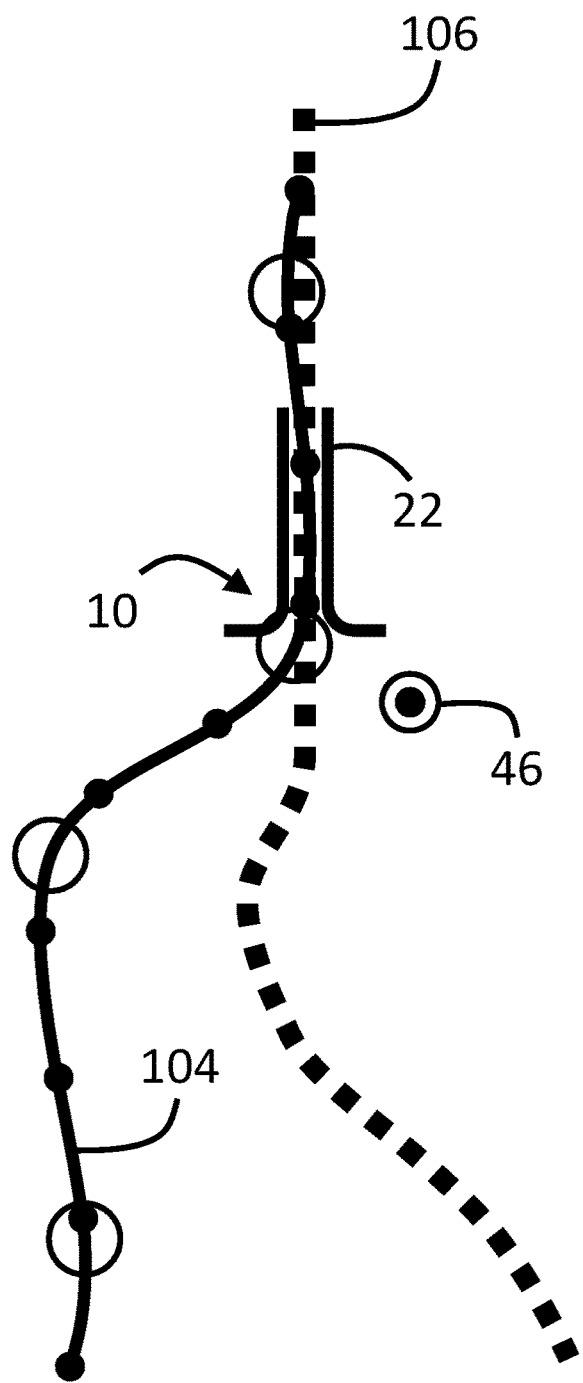
Figure 15L:
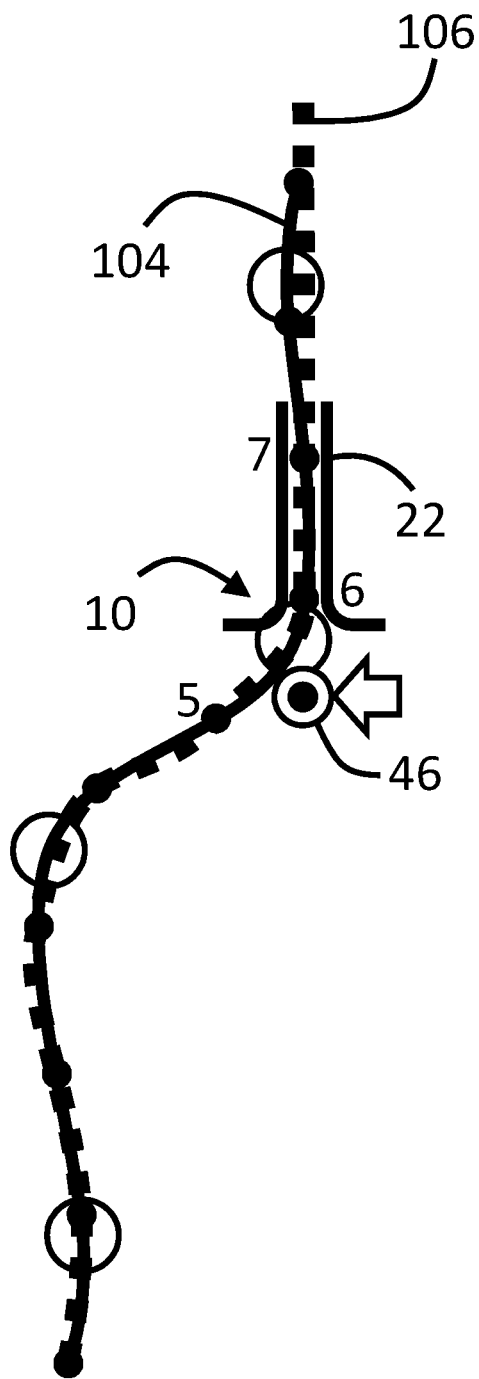
Figure 15M:
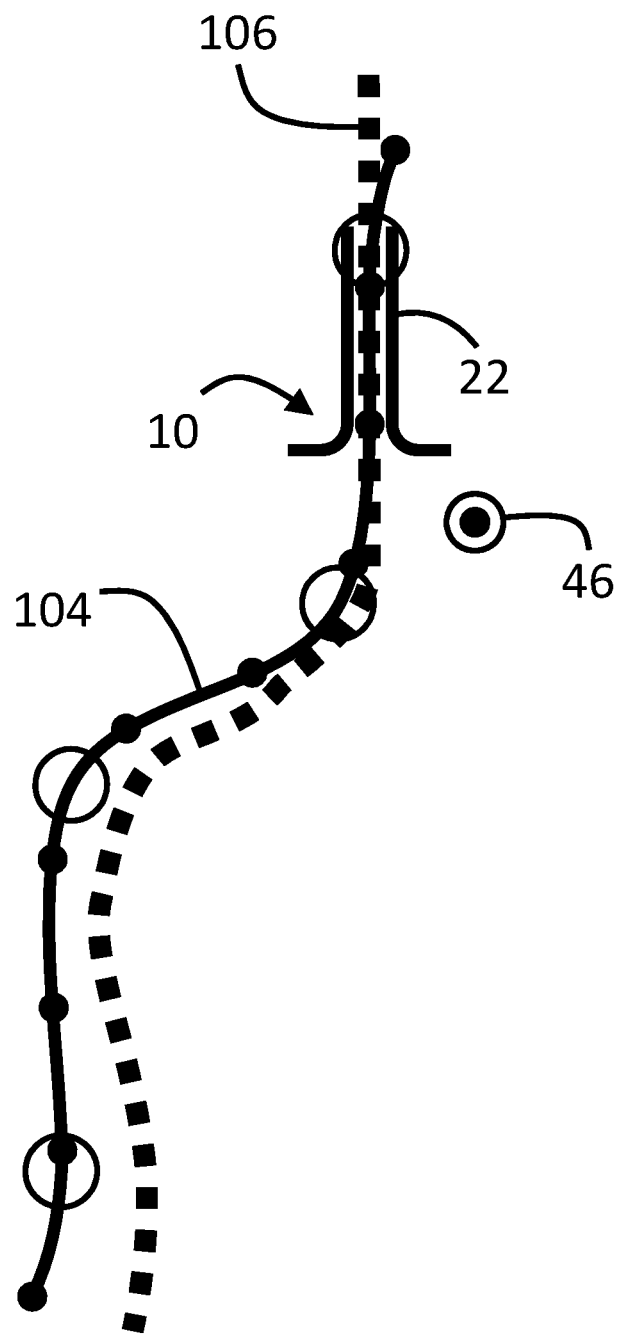
Figure 15N:
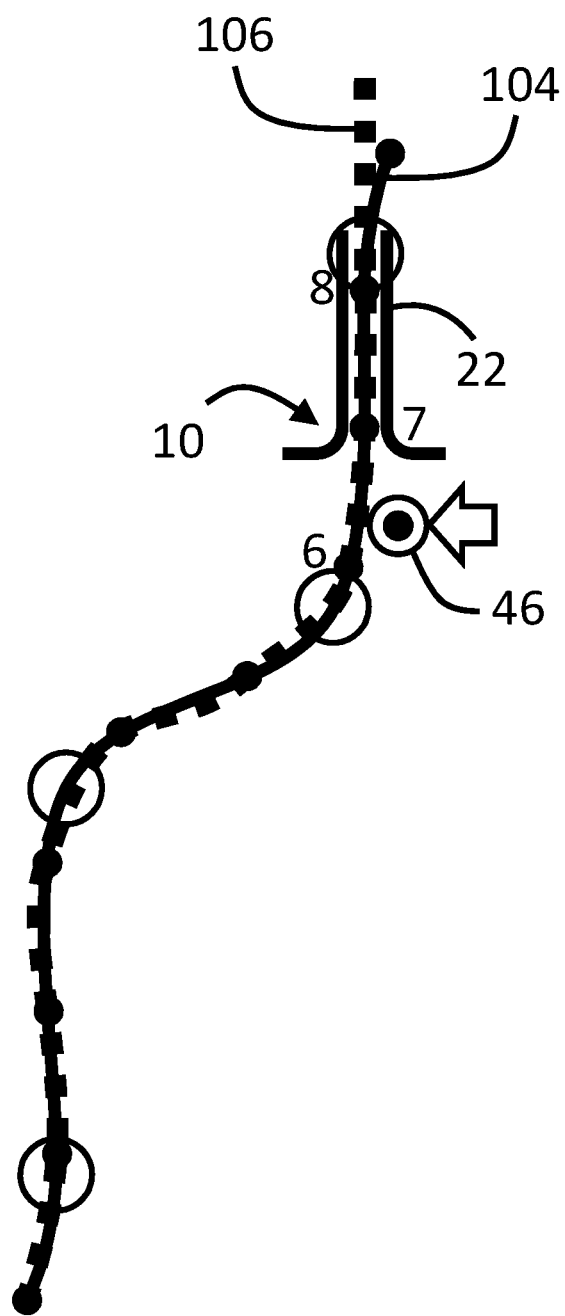
Figure 15O:
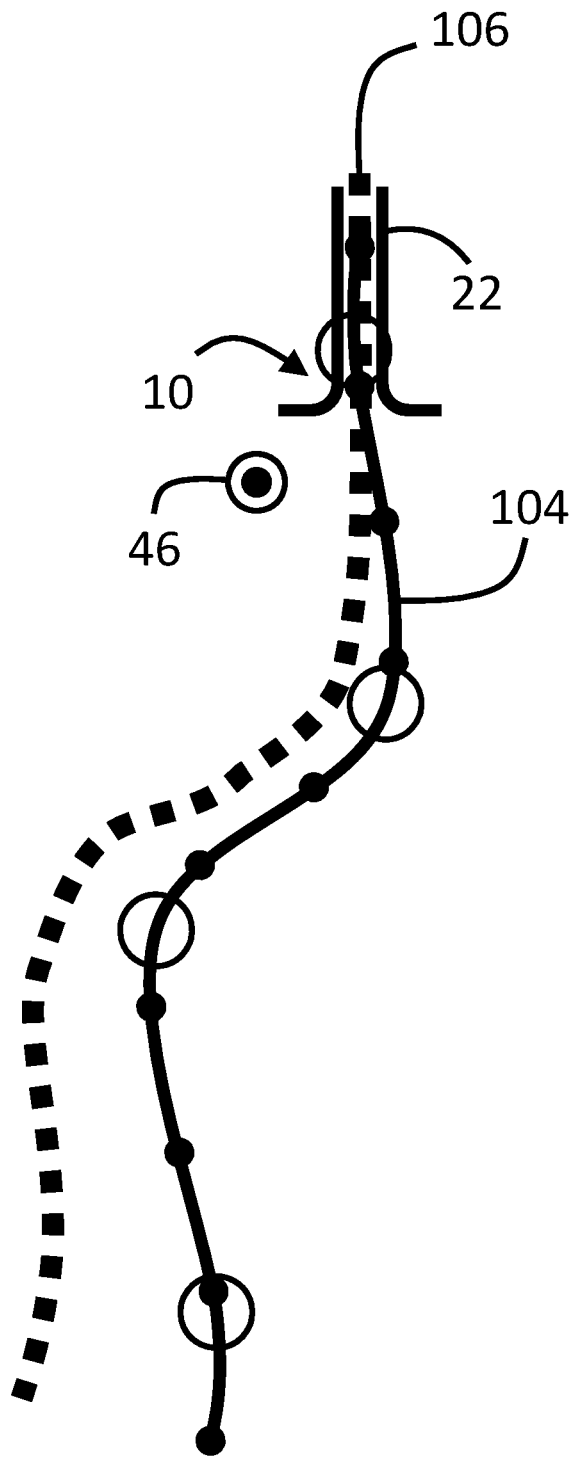
Figure 15P:
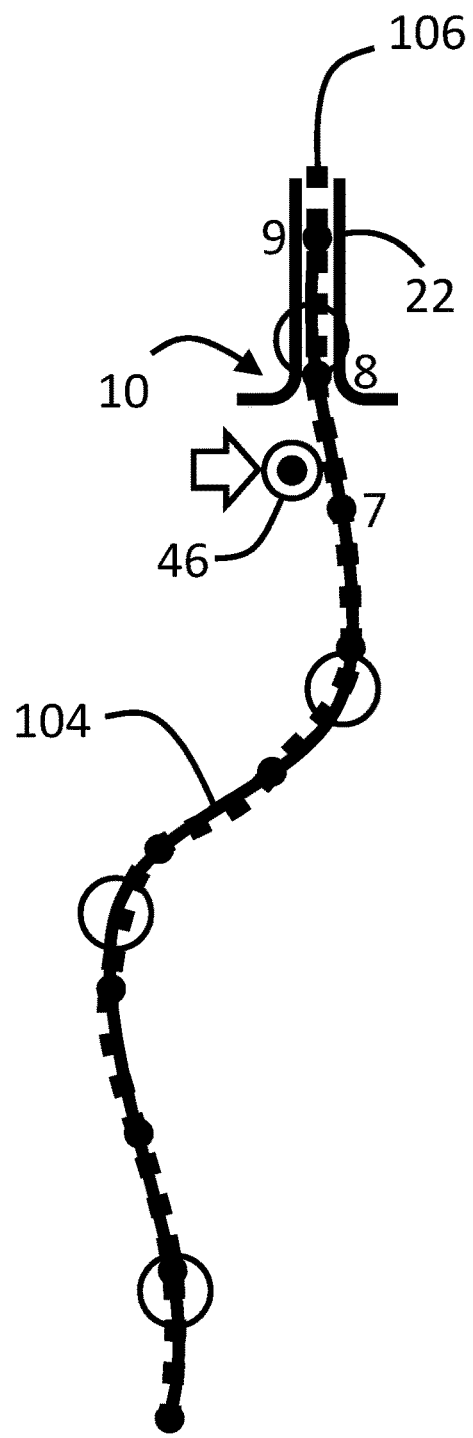
Figure 16:
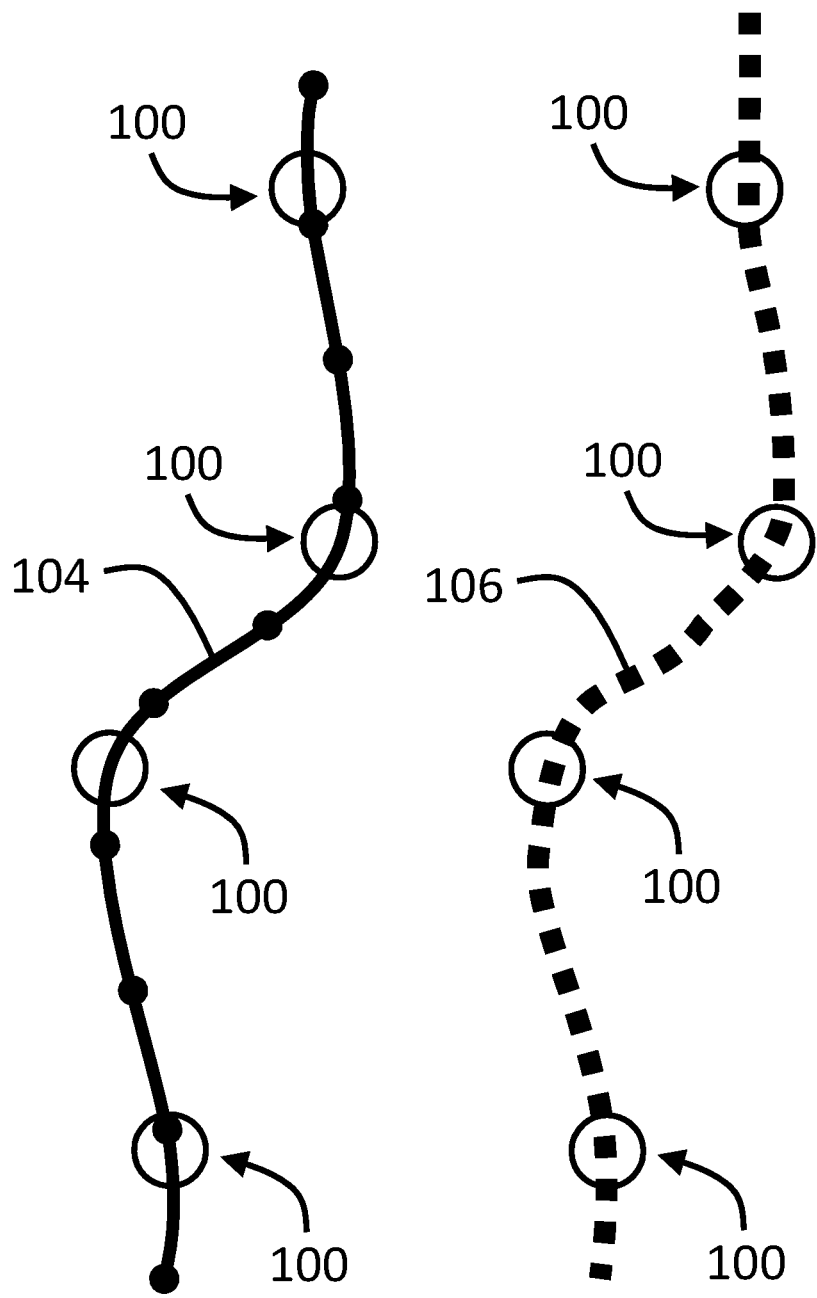
FIG. 16 is a schematic illustration comparing the planned spline to the fitted rod after completing the bending sequence of FIG. 15.

Referring now to FIGS. 15A-15P, with the planning illustrated with respect to FIGS. 12-14 in place, a rod 106 can be fed through the above-described system 10. At each increment, a bend is made by the system 10 to keep the rod 106 aligned with the spline 104 along the points 0-9 upon exit from the system 10. In this two-dimensional dimensional example, the bending roller 46 moves toward the right or the left to bend the rod in the plane drawn. In a three-dimensional implementation, the rotational movement device 16 would orient the rod 106 to be bent in any plane. Note that each bend generally creates an angle between two line segments defined by the points 0-9. For example, angles can be measured between points 1, 2, and 3, to form 1-2-3 angle, between points 2, 3, and 4 to form 2-3-4 angle, and so on. By holding the line segment of higher numbering in the rod guide 22 of the system 10, which acts as a straight collar, and applying a bend on a given line segment of the lower numbering using the bending roller 46, each angle can be created. For example, as illustrated in FIGS. 15C and 15D, the 1-2-3 angle is created by holding 2-3 straight and applying a bending force on 1-2. This same process can be applied for the 2-3-4 angle, as illustrated in FIGS. 15E and 15F, and each additional angle, as illustrated in FIGS. 15G through 15P, until, as illustrated in FIG. 16, the rod has been bent in a manner that matches the planned spline and layout of points 0-9 illustrated in FIGS. 13 and 14.

Figure 17:
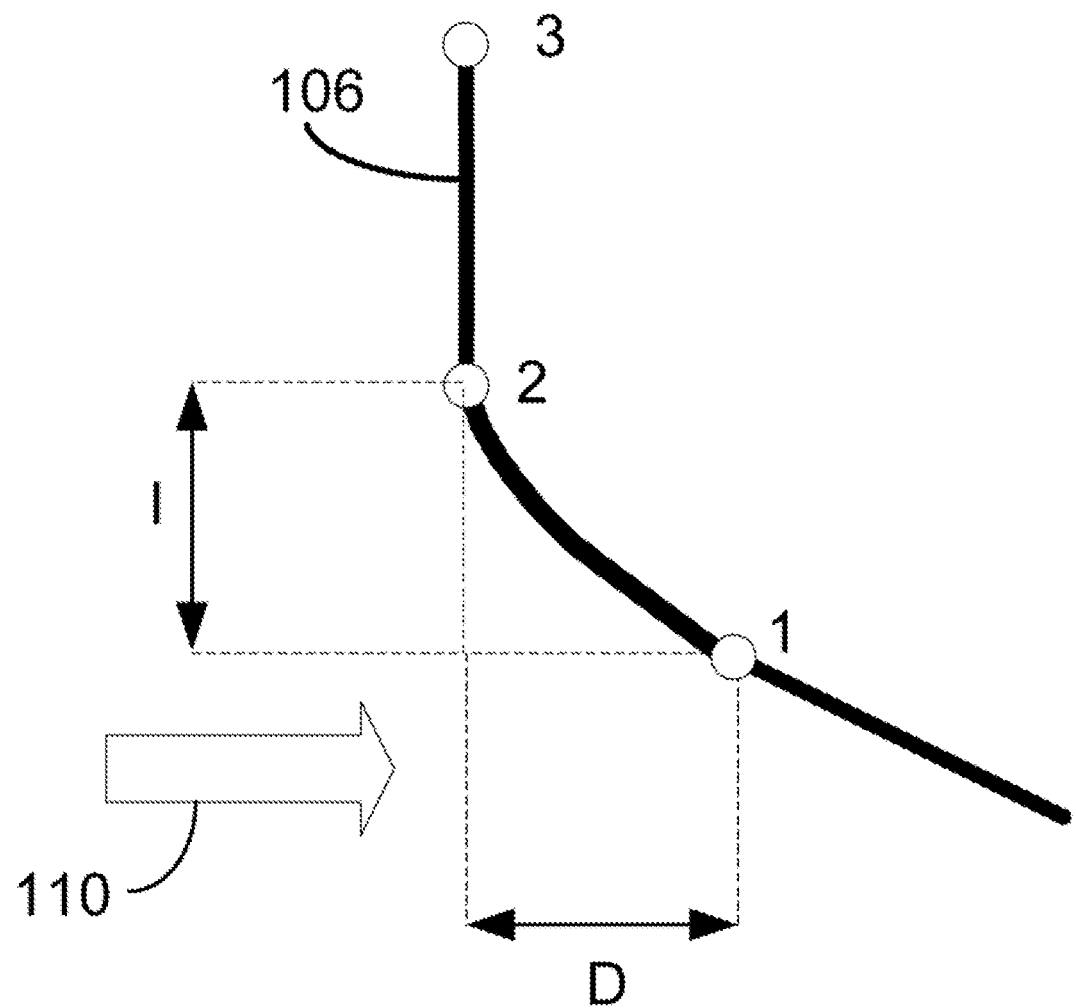
FIG. 17 is a schematic illustration of a rod being bent in accordance with the present invention.

Notably, the above-described process of bending alters the distance between points 0-9 as the rod 106 is bent and, to provide the results illustrated, these changes can be accounted for, as will be described. In particular, referring to FIG. 17, when the system applies a lateral bend along the direction indicated by arrow 110, below point 2, it changes the 1-2 segment from a straight line to a curved line. The change from straight line to curved line means path length is increased over a path in which a straight line segment connects points 1 and 2. Knowledge of the distance from point 1 to point 2 is desirable because the bend in this example is intended to position the 2-3 segment relative to what has already been bent below it. However, by the nature of the rod bending mechanism with the rod 106 gripped above and the bend occurring below point 2, the distance from point 2 to point 3 is fixed while the distance from point 1 to point 2 is not fixed. As a result, the amount of path length lost by bending must be predicted and added to an interval "I" between bend points on the rod 106 considered while it is straight (i.e., the incremental rod feed distance) by taking into account a push travel distance "D."

Figure 18:
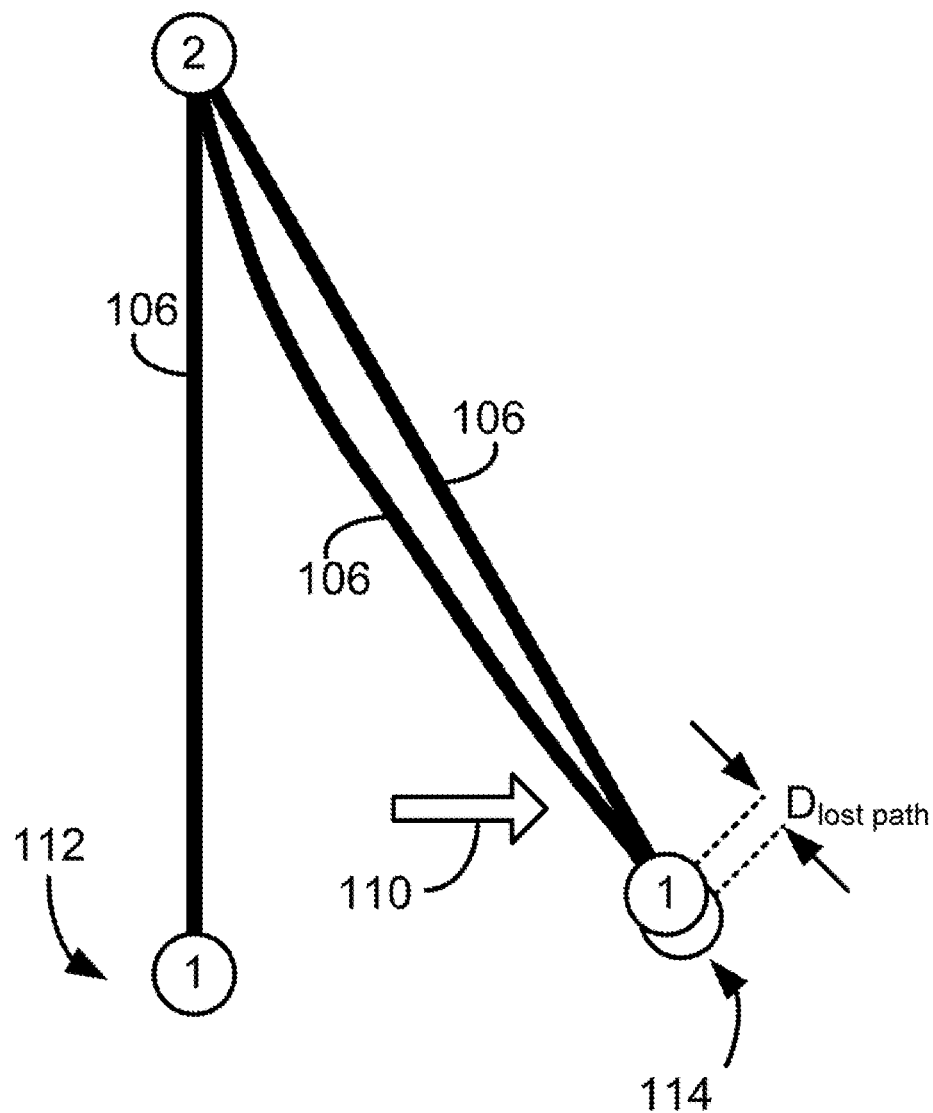
FIG. 18 is a schematic illustration of determining a lost path distance in accordance with the present invention.

In particular, this concept is further illustrated with respect to FIG. 18. In FIG. 18, a bend is to be created by pushing point 1 from position 112 in the direction of arrow 110 to position 114, while holding point 2 stationary. However, when the rod 106 is bent to move point 1 to position 114, the bend in the rod 106 forms an arc instead of following a straight path between point 1 and point 2, creating a lost path of distance "D" or a $D_{lost\ path}$. The lost path length can be a function of the bend angle (or pusher/roller linear travel), radius of curvature of the support (such as the flared base 56), and the composition and diameter of the rod material being bent. Therefore, an efficient way to incorporate the multiple factors into the calculation is to experimentally determine the relationship and apply it during automated bends. That is, a function "F" can be created for each type of rod being bent that satisfies:

$$D_{lost\ path} = F(\text{pusher travel})$$

For example, an operator can select the type of rod being bent and the radius of curvature of the support (if the support is interchangeable) and the controller can utilize a stored function for that material. With respect to stored functions, lost path distances may assessed experimentally at multiple pusher travels and a function can be fit to a resulting data set, which can then be stored for use by the controller. Such experiments can account for both lost path and bending recoil (discussed below) at the same time.

For example, a user can calibrate the system using a test rod similar or identical to the rod to be bent. The test rod can be inserted in the system and a bend applied using a set pusher travel distance. The test rod is fed forward by a set distance and another bend applied is applied using another set pusher travel distance. This process is repeated until the entire length of rod is used. Before applying bends or thereafter, optical tracking markers such as reflective spheres or infrared-emitting diodes that are trackable with high precision may be affixed on the test rod. Using tracking cameras to track the 3D locations of the tracking markers, points at which markers are attached can be stored to computer memory. The stored optical marker positions can be used to measure the bends, or the bend angle. Alternately, bent rods could be analyzed using optical analysis methods, such as photographing the rod against a grid background and counting rise over run, using a compass, or using a goniometer. An experiment such as described here need only be performed in a single bending plane to create suitable functions that are applicable in controlling 3D bending.

An example of usage of lost path distance is as follows. Starting with a straight rod 106 and in creating a bend of the line segment 1-2-3 in FIG. 17 sufficient for the rod 106 to match the planned spline, the flared base is positioned such that the flare initiates adjacent to point 1 on the rod 106. The rod 106 is then advanced downward by an interval (I), such that the point of initiation of the flare is adjacent to point 2 on the rod 106. For an applied lateral force to the rod 106 at this position, the distance (D) that the rod 106 must be pushed before point 1 intersects with the spline curve is known from the spline equation. In this position, if the rod 106 were theoretically infinitely flexible and there was zero flare at the base, the rod 106 would bend at a sharp corner adjacent to point 2 and the distance from point 1 to point 2 would be the hypotenuse of the triangle having a side of height I and a base of width D. Note that D and I are interrelated; as D increases, I decreases. In reality, the rod 106 is not infinitely flexible and the base has a flare; therefore the lost path for the distance D traveled by the pusher is known from the experiment. This lost path distance can be accounted for by simply advancing the rod 106 by this amount, i.e., adding $D_{lost\ path}$ to I. Alternately, a point on the spline can be calculated that has a path length exactly $D_{lost\ path}$ farther up the spline toward point 2. After increasing I or reassessing D to account for lost path and applying a lateral force to cause displacement D, the final resting location of point 1 on the rod 106 will be at the target position. That is, the actual shape of the rod 106 at all points between points 1 and 3 will be undetermined and will be dependent on material properties of the rod 106 and geometry of the base, but the specific points 1, 2, and 3 on the rod 106 will exactly intersect with the spline.

Figures 19A, 19B, 19C:
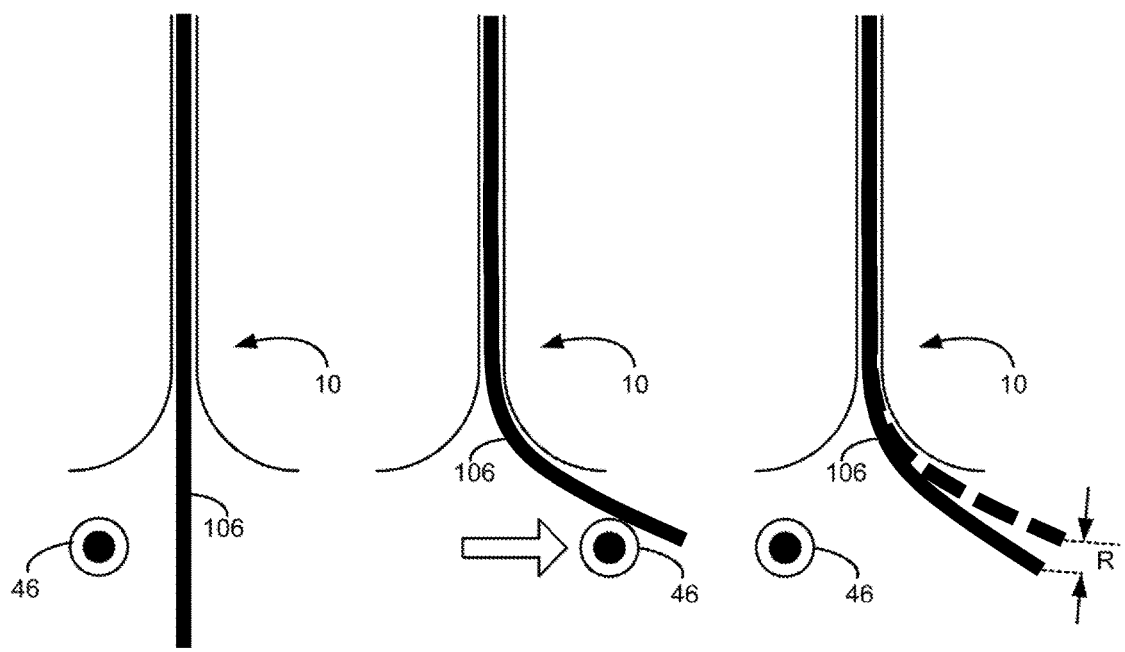
FIGS. 19A-19C are schematic illustrations of determining a recoil in accordance with the present invention.

Another variable that may be considered is bending recoil. Specifically, referring to FIGS. 19A-19O, the bend achieved when the pusher/roller element 46 is in contact with the rod 106 will not be the final bend achieved when the roller 46 is removed. Specifically, as illustrated in FIG. 19A, before the roller 46 engages the rod 106, the rod 106 is straight. The roller 46, as shown in FIG. 19B, engages the rod 106 and pushes it to an extreme angle. However, as illustrated in FIG. 19C, after the roller 46 disengages and is no longer applying a bend to the rod 106, the rod 106 will recoil to some extent but will retain a permanent bend. The amount of recoil "R" will depend upon material properties of the rod 106, such as ductility, elasticity, and the like, as well as geometry of the rod 106, such as diameter, cross-section, surface pattern, and the like. Some estimates of recoil "R" may be determined theoretically from geometry and material. However, the most reliable method for assessing and accounting for recoil "R" is using an experiment, such as described above with respect to lost path distance. Such experiments can be used to establish the relationship between pusher travel and actual bend achieved for a particular rod 106.

It should be apparent to those skilled in the art that the fit between intended curve and actual curve can be improved by decreasing the incremental rod feed distance (using a greater number of discrete points). However, if the incremental rod feed distance is less than the distance from the initiation of the flare to the contact point on the lateral pusher wheel, it becomes more complicated to predict the bending because the previous residual bend may have left the rod in a position where it comes into contact with the pusher wheel at a position offset from center. By the pusher contacting the already-bent rod sooner or later than it would have contacted a straight rod, over- or underbending might occur, unless effort is made to account for the previous bend. Detecting contact of the pusher with the rod allows the contact position to be uniquely determined for every bend and overcomes this issue. Non limiting examples of mechanisms for detecting contact of the pusher with the rod include optical sensors detecting physical gap between pusher and rod, electrical conductivity or resistivity measurement methods, detecting flow of electricity between the rod and the pusher wheel, or force sensing such as strain gauges to measure force of the pusher against the rod.

In summary, at each bend increment, the system can determine how far a previous bend point on the rod needs to be displaced laterally by the pusher, as shown in FIGS. 12-16. Using functions that are experimentally determined, the system can assess the pusher travel needed and the additional incremental rod feed needed so that this point is appropriately displaced to the desired position. By performing this procedure sequentially over the rod, it is possible to fit the incremental points exactly to the plan. In some cases, portions of the bent rod corresponding to portions of the spline curve between the discrete points may not overlay exactly with the spline, but the general rod shape should be excellent for interconnecting screw heads.

This application also incorporates by references herein in its entirety, pending PCT Application No. WO 2013/085982.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for bending a rod configured to be implanted into a patient, the method comprising:
   determining a shape for the rod to be formed into to allow the rod to be implanted into a patient;
   determining a plurality of pedicle points along the rod where pedicle screws will attach the rod to the patient when the rod is in the shape;
   determining a plurality of intermediate points along the rod and between the plurality of pedicle points;
   identifying a plurality of line segments defined by adjacent ones of the plurality of pedicle points and the plurality of intermediate points;
   determining an angle measurement to be formed at bend points between adjacent ones of the plurality of line segments to form the rod into the shape;
   determining bending parameters, using a lost path distance that accounts for a lost distance between adjacent bend points caused by curvature of the rod during bending of the rod into the shape, to perform on the rod to form the angle measurement between the adjacent ones of the plurality of line segments;
   feeding the rod into a bending system configured to bend the rod into the shape using the bending parameters, and controlling the bending system to bend the rod at the bend points such that the rod is bent into the shape according to the bending parameters such that the rod follows the plurality of line segments and angle measurements to intersect the plurality of pedicle points and plurality of intermediate points.

2. The method of claim 1 wherein determining the bending parameters includes identifying an amount of recoil.

3. The method of claim 2 wherein the amount of recoil is based on a relationship between a pusher travel against the rod of a pusher that bends the rod when in the bending system and an actual bend achieved in the rod, the relationship being experimentally determined using a test rod similar or identical to the rod to be bent.

4. The method of claim 1 wherein feeding the rod into the bending system includes rotating the rod relative to a bending device.

5. The method of claim 4 wherein the rotating includes at least one of a positive rotation between zero degrees and 180 degrees and a negative rotation between zero degrees and 180 degrees.

6. The method of claim 1 wherein determining the bending parameters includes optically scanning a surrogate rod to determine a proposed curvature of the rod.

7. The method of claim 6 further comprising physically manipulating the surrogate rod to the shape and applying identifiers to the surrogate rod prior to optically scanning the surrogate rod.

8. The method of claim 1 wherein determining the bending parameters includes using a digitizing probe to identify key points along the patient's spine and defining a proposed curvature of the rod based on the identified key points.

9. The method of claim 1 wherein determining the bending parameters includes predicting an amount of recoil based on at least one of material properties of the rod and geometry of the rod.

10. The method of claim 9 wherein the material properties includes at least one of ductility and elasticity and the geometry includes at least one of diameter and cross-section.

11. The method of claim 1 wherein the lost path distance is a function of one or more of the angle measurement, a linear travel of a roller configured to bend the rod within the bending system, a curvature of a support against which the rod is bent within the bending system, a composition of the rod, and a diameter of the rod.

12. A method for bending a rod configured to be implanted into a patient, the method comprising:
determining a shape for the rod to be formed into to allow the rod to be implanted into a patient;
identifying a plurality of line segments along the rod that define the shape of the rod to be formed;
determining an angle measurement to be formed between adjacent ones of the plurality of line segments to form the rod into the shape;
determining bending parameters to perform on the rod to form the angle measurement between the adjacent ones of the plurality of line segments;
feeding the rod in a first direction into a bending system configured to bend the rod into the shape using the bending parameters;
moving a roller of the bending system in a second direction perpendicular to the first direction to impose bending forces against the rod according to the bending parameters to bend the rod into the shape such that the rod follows the plurality of line segments and angle measurements; and
moving a cutting device in a third direction perpendicular to the first direction and opposite the second direction to cut the rod which is bent into the shape from the rest of the rod, wherein the cutting device is fixed relative to the roller such that movement of one of the cutting device and the roller results in movement of the other of the cutting device and the roller.

13. The method of claim 12 and further comprising:
determining a plurality of pedicle points along the rod where pedicle screws will attach the rod to the patient when the rod is in the shape; and
determining a plurality of intermediate points along the rod and between the plurality of pedicle points,
wherein the plurality of line segments are defined by adjacent ones of the plurality of pedicle points and the plurality of intermediate points.

14. The method of claim 12 wherein determining the bending parameters includes identifying an amount of recoil.

15. The method of claim 14 wherein the amount of recoil is based on a relationship between a travel distance of the roller against the rod and actual bend achieved by the rod, the relationship being experimentally determined using a test rod similar or identical to the rod to be bent.

16. The method of claim 12 wherein feeding the rod into the bending system includes rotating the rod relative to a bending device.

17. The method of claim 16 wherein the rotating includes at least one of a positive rotation between zero degrees and 180 degrees and a negative rotation between zero degrees and 180 degrees.

18. The method of claim 12 wherein determining the bending parameters includes optically scanning a surrogate rod to determine a proposed curvature of the rod.

19. The method of claim 12 wherein determining the bending parameters includes using a digitizing probe to identify key points along the patient's spine and defining a proposed curvature of the rod based on the identified key points.

20. The method of claim 12 wherein determining the bending parameters includes predicting an amount of recoil based on at least one of material properties of the rod and geometry of the rod, the material properties including at least one of ductility and elasticity and the geometry includes at least one of diameter, and cross-section.

* * * * *

UNITED STATES PATENT AND TRADEMARK OFFICE
CERTIFICATE OF CORRECTION

PATENT NO. : 10,194,968 B2  
APPLICATION NO. : 15/839319  
DATED : February 5, 2019  
INVENTOR(S) : Neil R. Crawford et al.

Page 1 of 1

It is certified that error appears in the above-identified patent and that said Letters Patent is hereby corrected as shown below:

In the Specification

Column 9, Lines 58-59, "two-dimensional dimensional" should be --two-dimensional--.

Column 11, Line 47, "19A-190" should be --19A-19C--.

Signed and Sealed this
Ninth Day of April, 2019

Andrei Iancu
*Director of the United States Patent and Trademark Office*